US007786349B2

(12) United States Patent
De Block

(10) Patent No.: US 7,786,349 B2
(45) Date of Patent: Aug. 31, 2010

(54) METHODS AND MEANS FOR INCREASING THE TOLERANCE OF PLANTS TO STRESS CONDITIONS

(75) Inventor: Marc De Block, Merelbeke (BE)

(73) Assignee: Bayer Bioscience N.V., Ghent (BE)

( * ) Notice: Subject to any disclaimer, the term of this patent is extended or adjusted under 35 U.S.C. 154(b) by 0 days.

(21) Appl. No.: 10/552,552

(22) PCT Filed: Apr. 9, 2004

(86) PCT No.: PCT/EP2004/003995

§ 371 (c)(1),
(2), (4) Date: Oct. 7, 2005

(87) PCT Pub. No.: WO2004/090140

PCT Pub. Date: Oct. 21, 2004

(65) Prior Publication Data

US 2006/0185038 A1 Aug. 17, 2006

Related U.S. Application Data

(60) Provisional application No. 60/496,688, filed on Aug. 21, 2003.

(30) Foreign Application Priority Data

Apr. 9, 2003 (EP) .................................. 03076044

(51) Int. Cl.
*C12N 15/82* (2006.01)

(52) U.S. Cl. ...................................... 800/285

(58) Field of Classification Search ........................ None
See application file for complete search history.

(56) References Cited

U.S. PATENT DOCUMENTS

| 6,395,543 B1 * | 5/2002 | Jacobson et al. ............. 435/375 |
| 2002/0040490 A1 * | 4/2002 | Gorlach et al. .............. 800/288 |

FOREIGN PATENT DOCUMENTS

| WO | WO 89/03887 | 5/1989 |
| WO | WO 89/10396 | 11/1989 |
| WO | WO 92/13956 | 8/1992 |
| WO | WO 96/06932 | 3/1996 |
| WO | WO 97/13865 | 4/1997 |
| WO | WO 99/53050 | 10/1999 |
| WO | WO 00/01133 | 1/2000 |
| WO | WO 00/04173 | 1/2000 |
| WO | WO0300898 | * 1/2000 |
| WO | WO 00/63397 | 10/2000 |
| WO | WO 01/12824 | 2/2001 |
| WO | WO 01/75167 | 10/2001 |
| WO | WO 02/13964 | 2/2002 |
| WO | WO 02/059294 | 8/2002 |
| WO | WO 03/000898 | 1/2003 |
| WO | WO 03/008540 | 1/2003 |
| WO | WO 03/52108 | 6/2003 |

OTHER PUBLICATIONS

Carthew et al. (Current Opinion in Cell Biology, 13:244-248, 2001).*
Arziman et al. (Nucleic Acids Research, 33:582-588, 2005).*
Elomaa et al. (Molecular Breeding, 2:41-50, 1996).*
Colliver et al. (Plant molecular Biology, 35:509-522, 1997).*
Bruening (Proc. Natl. Acad. Sci., 95:13349-13351, 1998).*
Mittler et al. (Trends in Plant Science, 11:15-19, 2006).*
Logemann et al. (PNAS, 99:2428-2432, 2002).*
Wesley et al. (The Plant Journal, 27:581-590, 2001).*
An et al. "Conserved Expression of the Arabidopsis ACT1 and ACT3 Actin Subclass in Organ Primordia and Mature Pollen," The Plant Cell, vol. 8, pp. 15-30, 1996.
De Block et al. "A Simple and Robust in Vitro Assay to Quantify the Vigour of Oilseed Rape Lines and Hybrids," Plant Physiology and Biochemistry, vol. 40, pp. 845-852, 2002.
Filipovic et al. "Inhibition of PARP Prevents Oxidant-Induced Necrosis but not Apoptosis in LLC-$PK_1$ Cells," Role of PARP in $H_2O_2$-Induced Cell Death, pp. F428-F436, 1999.
Harpster et al. "Relative Strengths of the 35S Califlower Mosiac Virus, 1', 2', and Nopaline Synthase Promoters in Transformed Tobacco Sugarbeet and Oilseed Rape Callus Tissue," Mol. Gen. Genet., vol. 212, pp. 182-190, 1988.
Hudspeth et al. "Structure and Expression of the Maize Gene Encoding the Phosphoenolypyruvate Carboxylase Isozyme in $C_4$ Photosynthesis," Molecular Biology, vol. 12, pp. 579-589, 1989.
Karp et al. "Simultaneous Extraction and Combined Bioluminescent Assay of $NAD^+$ and NADH," Analytical Biochemistry, vol. 128, pp. 175-180, 1983.
Keil et al. "Both Wound-Inducible and Tuber-Specific Expression are Mediated by the Promoter of a Single Member of the Potato Proteinase Inhibitor II Gene Family," The EMBO Journal, vol. 8, No. 5, pp. 1323-1330, 1989.
Keller et al. "Glycine-Rich Wall Proteins in Bean: Gene Structure and Association of the Protein with the Vascular System," The Embo Journal, vol. 7, No. 12, pp. 3625-3633, 1988.
Keller et al. "Specific Expression of a Novel Cell Wall Hydroxyproline-rich Glycoprotein Gene in Lateral Root Intitiation," Genes and Development, vol. 3, pp. 1639-1646, 1989.
Maes et al. "Plant Tagnology," Trends in Plant Science, vol. 4, No. 3, pp. 90-96, 1999.
McCallum et al. "Targeting Induced Local Lesions IN Genomes (Tilling) for Plant Functional Genomics," Plant Physiology, vol. 123, pp. 439-442, 2000.
Peleman et al. "Structure and Expression Analyses of the S-adenosylmethionine Synthetase Gene Family in *Arabidopsis thaliana*," pp. 359-369, Elsevier Science Publishers B.V., 1989.
Ying et al. "The Poly(ADP-Ribose) Glycohydrolase Inhibitor Gallotannin Blocks Oxidative Astrocyte Death," Neuropharmacology NeuroReport, vol. 11, No. 7, pp. 1385-1388, 2000.
Ying et al. "Poly(ADP-ribose) glycohydrolase mediates oxidative and excitotoxic neuronal death." *PNAS* (Oct. 9, 2001) 98(21): 12227-32.
Panda et al. "tej Defines a Role for Poly(ADP-Ribosyl)ation in Establishing Period Length of the Arabidopsis Circadian Oscillator." *Developmental Cell* (Jul. 2002) 3: 51-61.
Rawyler et al. "Membrane Lipid Integrity Relies on a Threshold of ATP Production Rate in Potato Cell Cultures Submitted to Anoxia." *Plant Physiol.* (May 1999) 120: 293-300.

* cited by examiner

*Primary Examiner*—Vinod Kumar
(74) *Attorney, Agent, or Firm*—Hunton & Williams LLP

(57) ABSTRACT

Methods and means are provided to increase the tolerance of plants to abiotic stress or adverse growing conditions, including drought, high light intensities, high temperatures, nutrient limitations and the like by reducing the activity of endogenous PARG proteins in plants.

1 Claim, 3 Drawing Sheets

METHODS AND MEANS FOR INCREASING THE TOLERANCE OF PLANTS TO STRESS CONDITIONS

CROSS-REFERENCE TO RELATED APPLICATIONS

This application is a U.S. national phase application of International PCT Application No. PCT/EP04/003995, filed Apr. 9, 2004, which claims the benefit under 35 U.S.C. 119 (a)-(d) to European Application No. 03076044.1, filed Apr. 9, 2003, and claims the benefit under 35 U.S.C. 119(e) to U.S. Provisional Application No. 60/496,688, filed Aug. 21, 2003, the disclosures of each of which are herein incorporated by reference in their entireties.

FIELD OF THE INVENTION

The present invention relates to the use of poly (ADP-ribose) glycohydrolases in plants to increase the tolerance of plants to adverse growing conditions, including drought, high light intensities, high temperatures, nutrient limitations and the like. Methods and means are provided to produce plants that are tolerant to abiotic stress conditions.

DESCRIPTION OF THE RELATED ART

Frequently, abiotic stress will lead either directly or indirectly to damage of the DNA of the cells of the plants exposed to the adverse conditions. Genomic damage, if left unrepaired, can lead to cell death. Tolerance to stress conditions exhibited by plants is the result of the ability of the plant cells exposed to the adverse conditions to reduce and/or repair the damage, and to survive.

Plant cells, like other eukaryotic cells, have evolved an elaborate DNA repair system. The activation of poly(ADP-ribose) polymerase (PARP) by DNA strand breaks is often one of the first cellular responses to DNA damage. PARP catalyzes the post-translational modification of proteins by adding successively molecules of ADP-ribose, obtained from the conversion of nicotineamide dinucleotide (NAD), to form multibranched polymers containing up to 200 ADP-ribose residues (about 40 residues in plants). The dependence of poly(ADP-ribose) synthesis on DNA strand breaks, and the presence of PARP in multiprotein complexes further containing key effectors of DNA repair, replication and transcription reactions, strongly suggests that this posttranslational modification is involved in metabolism of nucleic acids, and DNA repair. There are also indications that poly (ADP-ribose) synthesis is involved in regulation of cell cycle and cell death.

Poly (ADP-ribosylation) of proteins is transient in living cells. The poly (ADP-ribose) polymers are rapidly turned over, being converted to free ADP-ribose by the exoglycosidase and endoglycosidase activity of poly (ADP-ribose) glycohydrolase (PARG; E.C.3.2.1.143). The most proximal unit of ADP ribose on the protein acceptor is hydrolyzed by the action of another enzyme (ADP-ribosyl protein lyase).

In addition to this positive (DNA-repair associated) effect of PARP on cell survival, there is also a negative effect of PARP. The process of activating PARP upon DNA damage is associated with a rapid lowering of NAD+ levels, since each ADP-ribose unit transferred by PARP consumes one molecule of NAD+. NAD+ depletion in turn results in ATP depletion, because NAD+ resynthesis requires at least (depending on the biosynthesis pathway) three molecules of ATP per molecule of NAD+. Furthermore, NAD+ depletion block glyceraldehyde-3-phosphate dehydrogenase activity, which is required to resynthesize ATP during glycolysis. Finally, NAD+ is a key carrier of electrons needed to generate ATP via electron transport and oxidative phosphorylation.

The physiological consequence of NAD+ and ATP depletion has been established in the context of DNA-damage induced cell death. It has been shown that the completion of apoptosis is absolutely dependent on the presence of ATP and that, in the absence of this nucleotide, the type of cellular demise switches from apoptosis to necrosis. Since the cellular lysis associates with necrosis generates further damage to neighboring cells it is preferable for multicellular organisms to favor apoptotic cell death rather than necrosis.

It is thus very important to consider the delicate balance of positive and negative effects of the poly (ADP ribosyl)ation on the potential of a cell to survive DNA damage.

WO 00/04173 describes methods to modulate programmed cell death (PCD) in eukaryotic cells and organisms, particularly plant cells and plants, by introducing of "PCD modulating chimeric genes" influencing the expression and/or apparent activity of endogenous poly-(ADP-ribose) polymerase (PARP) genes. Programmed cell death may be inhibited or provoked. The invention particularly relates to the use of nucleotide sequences encoding proteins with PARP activity for modulating PCD, for enhancing growth rate or for producing stress tolerant cells and organisms.

PARG encoding genes have been identified in a number of animals such as *Rattus norvegicus* (Accession numbers: NM_031339, NW_043030, AB019366), *Mus musculus* (Accession numbers: NT_039598, NM_003631, AF079557), *Homo sapiens* (Accession numbers: NT_017696; NM_003631, AF005043), *Bos taurus* (Accession numbers: NM_174138, U78975) *Drosophila melanogaster* (Accession number: AF079556).

In plants, a poly(ADP-ribose) glycohydrolase has been identified by map-based cloning of the wild-type gene inactivated in a mutant affected in clock-controlled transcription of genes in *Arabidopsis* and in photoperiod dependent transition from vegetative growth to flowering (tej). The nucleotide sequence of the gene can be obtained from nucleotide databases under the accession number AF394690 (Panda et al., 2002 Dev. Cell. 3, 51-61).

SUMMARY AND OBJECTS OF THE INVENTION

The invention provides a method to produce a plant tolerant to stress conditions comprising the steps of providing plant cells with a chimeric gene to create transgenic plant cells, wherein the chimeric gene comprises the following operably linked DNA fragments: a plant-expressible promoter; a DNA region, which when transcribed yields an ParG inhibitory RNA molecule; and a 3' end region involved in transcription termination and polyadenylation. A population of transgenic plant lines is regenerated from the transgenic plant cell; and a stress tolerant plant line is identified within the population of transgenic plant lines. The ParG inhibitory RNA molecule may comprise a nucleotide sequence of at least 20 consecutive nucleotides of the nucleotide sequence of the ParG gene present in the plant cell (the endogenous ParG gene). The ParG inhibitory RNA molecule may also comprise a nucleotide sequence of at least 20 consecutive nucleotides of the complement of the nucleotide sequence of the ParG gene present in the plant cell (the endogenous ParG gene). In yet another embodiment, the parG inhibitory RNA may comprise a sense region comprising a nucleotide sequence of at least 20 consecutive nucleotides of the nucleotide sequence of the ParG gene present in the plant cell and an antisense region comprising a nucleotide sequence of at least 20 consecutive nucleotides of the complement of the nucleotide sequence of the ParG gene present in the plant cell, wherein the sense and antisense region are capable of forming a double stranded RNA region comprising said at least 20 consecutive nucleotides. The chimeric gene may further comprise a DNA region encoding a self-splicing ribozyme between said DNA region coding for parG inhibitory RNA molecule and the 3' end region. Stress conditions may be selected from heat, drought, nutrient depletion, oxidative stress or high light conditions.

In another embodiment of the invention, a method is provided to produce a plant tolerant to stress conditions comprising the steps of: isolating a DNA fragment of at least 100 bp comprising a part of the parG encoding gene of the plant of interest; producing a chimeric gene by operably linking a plant expressible promoter region to the isolated DNA fragment comprising part of the parG encoding gene of the plant in direct orientation compared to the promoter region; and to the isolated DNA fragment comprising part of the parG encoding gene of said plant in inverted orientation compared to the promoter region, and a 3' end region involved in transcription termination and polyadenylation. These chimeric genes are then provided to plant cells to create transgenic plant cells. A population of transgenic plant lines is regenerated from the transgenic plant cells; and a stress tolerant plant line is identified within the population of transgenic plant lines. The invention also relates to stress tolerant plant cells and plants obtained by this process.

In yet another embodiment of the invention, a method is provided to produce a plant tolerant to stress conditions comprising the steps of providing plant cells with a chimeric gene to create transgenic plant cells, comprising a DNA region, which when transcribed yields an ParG inhibitory RNA molecule, whereby the DNA region comprises a nucleotide sequence of at least 21 to 100 nucleotides of a nucleotide sequence encoding a protein comprising the amino acid sequence of SEQ ID No. 1, 2 or 16 or at least 21 to 100 nucleotides of a nucleotide sequence of SEQ ID No. 3, 4, 15 or 23 operably linked to a plant-expressible promoter and a 3' end region involved in transcription termination and polyadenylation; regenerating a population of transgenic plant lines from said transgenic plant cell; and identifying a stress tolerant plant line within the population of transgenic plant lines.

The invention also provides DNA molecules comprising a plant-expressible promoter, operably linked to a DNA region, which when transcribed yields an ParG inhibitory RNA molecule, and to a 3' end region involved in transcription termination and polyadenylation. The ParG inhibitory RNA molecule may comprise a nucleotide sequence of at least 20 consecutive nucleotides of the nucleotide sequence of the ParG gene present in the plant cell (the endogenous ParG gene). The ParG inhibitory RNA molecule may also comprise a nucleotide sequence of at least 20 consecutive nucleotides of the complement of the nucleotide sequence of the ParG gene present in the plant cell (the endogenous ParG gene). In yet another embodiment, the parG inhibitory RNA may comprise a sense region comprising a nucleotide sequence of at least 20 consecutive nucleotides of the nucleotide sequence of the ParG gene present in the plant cell and an antisense region comprising a nucleotide sequence of at least 20 consecutive nucleotides of the complement of the nucleotide sequence of the ParG gene present in the plant cell, wherein the sense and antisense region are capable of forming a double stranded RNA region comprising said at least 20 consecutive nucleotides. The chimeric gene may further comprise a DNA region encoding a self-splicing ribozyme between said DNA region coding for parG inhibitory RNA molecule and the 3' end region. The chimeric gene may also comprise a nucleotide sequence of at least 21 to 100 nucleotides of a nucleotide sequence encoding a protein comprising the amino acid sequence of SEQ ID No 1, 2 or 16 or at least 21 to 100 nucleotides of a nucleotide sequence of SEQ ID No. 3, 4, 15 or 23.

In yet another embodiment, the invention relates to plant cell comprising the DNA molecule of the invention and plants consisting essentially of such plant cells, as well as to processes for producing stress tolerant plants, comprising the step of further crossing such plants with another plant. Seeds and propagating material of such plants comprising the chimeric genes of the invention are also provided.

The invention also relates to a method for obtaining stress tolerant plants comprising the steps of subjecting a plant cell line or a plant or plant line, to mutagenesis; identifying those plant cells or plants that have a mutation in an endogenous ParG gene; subjecting the identified plant cells or plants to stress conditions and identifying plant cells or plants that tolerate said stress conditions better than control plants. Alternatively, plant cells or plants may be selected for resistance to ParG inhibitors and further treated as described in this paragraph.

The invention further relates to a stress tolerant plant cell or plant having a mutation in the endogenous ParG gene.

DETAILED DESCRIPTION OF PREFERRED EMBODIMENTS

The invention is based, on the one hand, on the demonstration that cells from stress resistant plant lines comprising a chimeric gene reducing the PARP gene expression, exhibited a higher NAD/ATP content under adverse conditions than cells from untransformed plant lines. On the other hand, it has been observed that silencing of the expression of PARG encoding gene in tobacco using a transient silencing RNA vector based on satellite viruses resulted in a similar phenotype as that observed for silencing of PARP encoding gene using the same silencing system. Furthermore, silencing the expression of PARG encoding gene in plants, such as *Arabidopsis* and tobacco, resulted in plants that were more resistant to stress conditions, such as e.g. those imposed by high light conditions.

Figure 1:
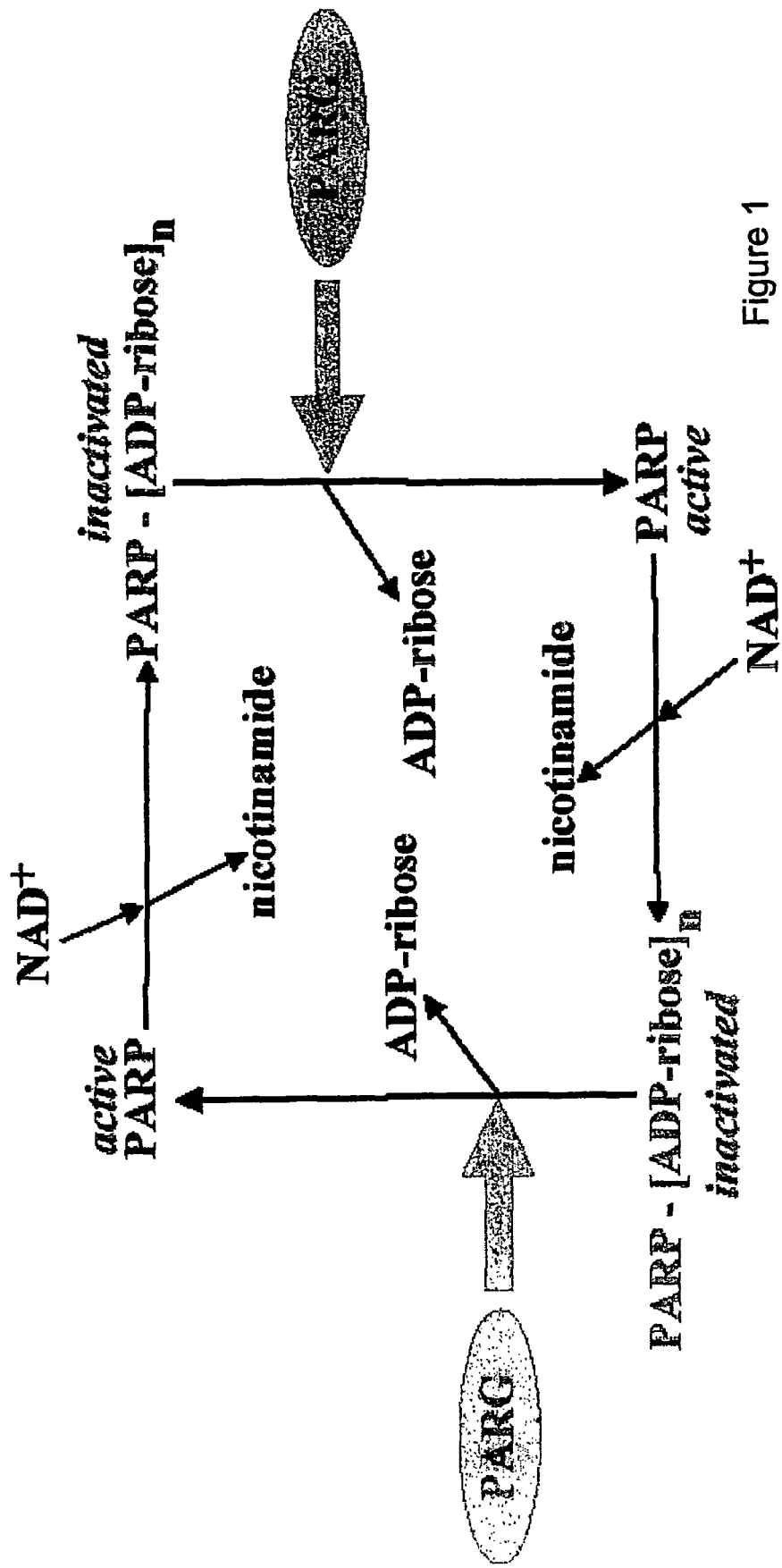
FIG. 1. Schematic representation of the poly-ADP ribose polymeratization/depolymerization cycle by the action of PARP/PARG in a eukaryotic cell.

Although not intending to limit the invention to a specific mode of action, it is expected that silencing of PARG gene expression results in a similar phenotype as silencing of PARP gene expression for the following reasons. As can be seen from FIG. 1, polymerization of ADP ribose catalyzed by PARP, consuming NAD, is followed by depolymerization of poly ADP ribose, catalyzed by PARG. Poly ADP ribosylation of the PARP protein itself results in inactivation of the PARP protein. The speed at which the ADP ribose polymerization/depolymerization cycle occurs in plant cells, leading to NAD depletion and consequently ATP depletion, can be slowed down or stopped by reduction of the PARP gene expression or of the enzymatic activity of PARP. As a result, plant cells, and plants comprising such cells are more resistant to adverse conditions. The data provided here indicate that a similar effect can be obtained through slowing down or stopping the cycle by reduction of the PARG gene expression or PARG activity.

The invention relates to reduction of plant cell death in response to adverse environmental conditions, and consequently to enhanced stress resistance, by altering the level of expression of ParG genes, or by altering the activity or the apparent activity of PARG proteins in that plant cell. Conveniently, the level of expression of ParG genes may be controlled genetically by introduction of chimeric genes altering the expression of ParG genes, or by altering the endogenous PARG encoding genes, including the expression signals.

In one embodiment of the invention, a method for producing plants tolerant to stress conditions or adverse growing conditions is provided comprising the steps of:
 providing plant cells with a chimeric gene to create transgenic plant cells, wherein the chimeric gene comprises the following operably linked DNA fragments:
  a plant-expressible promoter;
  a DNA region, which when transcribed yields a ParG inhibitory RNA molecule;
  a 3' end region involved in transcription termination and polyadenylation;
 regenerating a population of transgenic plant lines from said transgenic plant cell; and
 identifying a stress tolerant plant line within said population of transgenic plant lines.

As used herein "a stress tolerant plant" or "a plant tolerant to stress conditions or adverse growing conditions" is a plant (particularly a plant obtained according to the methods of the invention), which, when subjected to adverse growing conditions for a period of time, such as but not limited to drought, high temperatures, limited supply of nutrients (particularly nitrogen), high light intensities, grows better than a control plant not treated according to the methods of the invention. This will usually be apparent from the general appearance of the plants and may be measured e.g., by increased biomass production, continued vegetative growth under adverse conditions or higher seed yield. Stress tolerant plant have a broader growth spectrum, i.e. they are able to withstand a broader range of climatological and other abiotic changes, without yield penalty. Biochemically, stress tolerance may be apparent as the higher $NAD^+$-NADH/ATP content and lower production of reactive oxygen species of stress tolerant plants compared to control plants under stress condition. Stress tolerance may also be apparent as the higher chlorophyll content, higher photosynthesis and lower chlorophyll fluorescence under stress conditions in stress tolerant plants compared to control plants under the same conditions.

It will be clear that it is also not required that the plant be grown continuously under the adverse conditions for the stress tolerance to become apparent. Usually, the difference in stress tolerance between a plant or plant cell according to the invention and a control plant or plant cell will become apparent even when only a relatively short period of adverse conditions is encountered during growth.

As used herein, a "ParG inhibitory RNA molecule" is an RNA molecule that is capable of decreasing the expression of the endogenous PARG encoding genes of a plant cell, preferably through post-transcriptional silencing. It will be clear that even when a ParG inhibitory RNA molecule decreases the expression of a PARG encoding gene through post-transcriptional silencing, such an RNA molecule may also exert other functions within a cell, such as e.g. guiding DNA methylation of the endogenous ParG gene, again ultimately leading to decreased expression of the PARG encoding gene. Also, expression of the endogenous PARG encoding genes of a plant cell may be reduced by transcriptional silencing, e.g., by using RNAi or dsRNA targeted against the promoter region of the endogenous ParG gene.

As used herein, a "PARG encoding gene" or a "ParG gene" is a gene capable of encoding a PARG (poly ADP ribose glycohydrolase) protein, wherein the PARG protein catalyzes the depolymerization of poly ADP-ribose, by releasing free ADP ribose units either by endoglycolytic or exoglycolytic action.

PARG encoding genes may comprise a nucleotide sequence encoding a protein comprising the amino acid sequence of SEQ ID No. 1 (*Arabidopsis thaliana*) or of SEQ ID No. 2 (*Solanum tuberosum*) or of SEQ ID No. 16 (*Oryza sativa*) or parts thereof, such as a DNA fragment comprising the nucleotide sequence of SEQ ID No. 3 or SEQ ID No. 4 or SEQ ID No. 15. or SEQ ID No. 23 (*Zea mays*).

However, it will be clear that the skilled person can isolate variant DNA sequences from other plant species, by hybridization with a probe derived from the above mentioned PARG encoding genes from plant species, or even with a probe derived from the above mentioned PARG encoding genes from animal species. To this end, the probes should preferably have a nucleotide sequence comprising at least 40 consecutive nucleotides from the coding region of those mentioned PARG encoding genes sequences, preferably from the coding region of SEQ ID No 3 or SEQ ID No 4. The probes may however comprise longer regions of nucleotide sequences derived from the ParG genes, such as about 50, 60, 75, 100, 200 or 500 consecutive nucleotides from any of the mentioned ParG genes. Preferably, the probe should comprise a nucleotide sequence coding for one of the highly conserved regions of the catalytic domain, which have been identified by aligning the different PARG proteins from animals. These regions are also present in the identified PARG protein from *Arabidopsis thaliana* and comprise the amino acid sequence LXVDFANXXXGGG (SEQ ID No. 10 from the amino acid at position 1 to the amino acid at position 13; corresponding to SEQ ID No 1 from the amino acid at position 252 to the amino acid at position 264; X may be any amino acid) LXVDFANXXXGGGXXXXGXVQEEIRF (SEQ ID No. 10 from the amino acid at position 1 to the amino acid at position 26; corresponding to SEQ ID No 1 from the amino acid at position 252 to the amino acid at position 277) or LXVDFANXXXGGGXXXXGXVQEEIRFXXXPE (SEQ ID No. 10; corresponding to SEQ ID No 1 from the amino acid at position 252 to the amino acid at position 282), TGXWGCGXFXGD (SEQ ID No. 11 from the amino acid at position 1 to the amino acid at position 12; corresponding to SEQ ID No 1 from the amino acid at position 449 to the amino acid at position 460) or TGXWGCGAFXGDXXLKXXXQ (SEQ ID No. 11; corresponding to SEQ ID No 1 from the amino acid at position 449 to the amino acid at position 468). Other conserved regions have the amino acid sequence DXXXRXXXXAIDA (SEQ ID No. 12; corresponding to SEQ ID No 1 from the amino acid at position 335 to the amino acid at position 344) or REXXKAXXGF (SEQ ID No. 13; corresponding to SEQ ID No 1 from the amino acid at position 360 to the amino acid at position 369) or GXXXXSXYTGY (SEQ ID No. 14; corresponding to SEQ ID No 1 from the amino acid at position 303 to the amino acid at position 313). Hybridization should preferably be under stringent conditions.

"Stringent hybridization conditions" as used herein mean that hybridization will generally occur if there is at least 95% and preferably at least 97% sequence identity between the probe and the target sequence. Examples of stringent hybridization conditions are overnight incubation in a solution comprising 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared carrier DNA such as salmon sperm DNA, followed by washing the hybridization support in 0.1×SSC at approximately 65° C., e.g. for about 10 min (twice). Other hybridization and wash conditions are well known and are exemplified in Sambrook et al, Molecular Cloning: A Laboratory Manual, Second Edition, Cold Spring Harbor, N.Y. (1989), particularly chapter 11.

Alternatively, ParG encoding genes or parts thereof may also be isolated by PCR based techniques, using as primers oligonucleotides comprising at least 20 consecutive nucleotides from a nucleotide sequence of the mentioned PARG encoding genes or the complement thereof. Such primers may comprise a nucleotide sequence encoding a conserved region, as mentioned above, or be complementary to such a nucleotide sequence. Oligonucleotides which may be used for that purpose may comprise the nucleotide sequence of either or SEQ ID No. 5, SEQ ID No 6., SEQ ID No. 7 or SEQ ID No. 8. Oligonucleotides which may be used may also be degenerate, such as the oligonucleotide primers of SEQ ID No 17, SEQ ID No 18, SEQ ID No 19; SEQ ID No 20, SEQ ID No 21 or SEQ ID No 22.

Specific PCR fragments from ParG genes may e.g., be obtained by using combinations of the oligonucleotides having the nucleotide sequence of SEQ ID No. 5 and SEQ ID No 6 using e.g., *Arabidopsis* genomic DNA or cDNA as a template DNA, or by using combinations of the oligonucleotides having the nucleotide sequence of SEQ ID No. 7 and SEQ ID No 8 using e.g., potato genomic DNA or cDNA as a template DNA, under stringent annealing conditions.

The isolated sequences may encode a functional PARG protein or a part thereof. Preferably the isolated sequences should comprise a nucleotide sequence coding for one or more of the highly conserved regions from the catalytic domain of PARG proteins as mentioned elsewhere.

However, for the purpose of the invention is not required that the isolated sequences encode a functional ParG protein nor that a complete coding region is isolated. Indeed, all that is required for the invention is that a chimeric gene can be designed or produced, based on the identified or isolated sequence of the endogenous ParG gene from a plant, which is capable of producing a ParG inhibitory RNA. Several alternative methods are available to produce such a ParG inhibitory RNA molecule.

In one embodiment, the ParG inhibitory RNA molecule encoding chimeric gene is based on the so-called antisense technology. In other words, the coding region of the chimeric gene comprises a nucleotide sequence of at least 20 consecutive nucleotides of the complement of the nucleotide sequence of the endogenous ParG gene of the plant cell or plant, the expression of which is targeted to be reduced. Such a chimeric gene may be conveniently constructed by operably linking a DNA fragment comprising at least 20 nucleotides from the isolated or identified ParG gene, or part of such a gene, in inverse orientation, to a plant expressible promoter and 3'end formation region involved in transcription termination and polyadenylation. It will be immediately clear that there is no need to know the exact nucleotide sequence or complete nucleotide sequence of such a DNA fragment from an isolated ParG gene.

In another embodiment the ParG inhibitory RNA molecule encoding chimeric gene is based on the so-called co-suppression technology. In other words, the coding region of the chimeric gene comprises a nucleotide sequence of at least 20 consecutive nucleotides of the nucleotide sequence of the endogenous ParG gene of the plant cell or plant, the expression of which is targeted to be reduced. Such a chimeric gene may be conveniently constructed by operably linking a DNA fragment comprising at least 20 nucleotides from the isolated or identified ParG gene, or part of such a gene, in direct orientation, to a plant expressible promoter and 3'end formation region involved in transcription termination and polyadenylation. Again it is not required to know the exact nucleotide sequence of the used DNA fragment from the isolated ParG gene.

The efficiency of the above mentioned chimeric genes in reducing the expression of the endogenous ParG gene may be further enhanced by inclusion of DNA elements which result in the expression of aberrant, unpolyadenylated ParG inhibitory RNA molecules. One such DNA element suitable for that purpose is a DNA region encoding a self-splicing ribozyme, as described in WO 00/01133.

The efficiency or the above mentioned chimeric genes in reducing the expression of the endogenous ParG gene of a plant cell may also be further enhanced by including into one plant cell simultaneously a chimeric gene as herein described encoding a antisense ParG inhibitory RNA molecule and a chimeric gene as herein described encoding a sense ParG inhibitory RNA molecule, wherein said antisense and sense ParG inhibitory RNA molecules are capable of forming a double stranded RNA region by base pairing between the mentioned at least 20 consecutive nucleotides, as described in WO 99/53050.

As further described in WO 99/53050, the sense and antisense ParG inhibitory RNA regions, capable of forming a double stranded RNA region may be present in one RNA molecule, preferably separated by a spacer region. The spacer region may comprise an intron sequence. Such a chimeric gene may be conveniently constructed by operably linking a DNA fragment comprising at least 20 nucleotides from the isolated or identified endogenous ParG gene, the expression of which is targeted to be reduced, in an inverted repeat, to a plant expressible promoter and 3' end formation region involved in transcription termination and polyadenylation. To achieve the construction of such a chimeric gene, use can be made of the vectors described in WO 02/059294.

An embodiment of the invention thus concerns a method for obtaining a stress tolerant plant line comprising the steps of providing plant cells with a chimeric gene to create transgenic plant cells, wherein the chimeric gene comprises the following operably linked DNA fragments:
a plant-expressible promoter,
a DNA region, which when transcribed yields a ParG inhibitory RNA molecule comprising a nucleotide sequence of at least 20 consecutive nucleotides of the nucleotide sequence of the ParG gene present in said plant cell; or
a DNA region, which when transcribed yields a ParG inhibitory RNA molecule comprising a nucleotide sequence of at least 20 consecutive nucleotides of the complement of the nucleotide sequence of the ParG gene present in said plant cell; or a DNA region, which when transcribed yields a ParG inhibitory RNA molecule comprising a sense region comprising a nucleotide sequence of at least 20 consecutive nucleotides of the nucleotide sequence of the ParG gene present in said plant cell and an antisense region comprising a nucleotide sequence of at least 20 consecutive nucleotides of the complement of the nucleotide sequence of the ParG gene present in said plant cell, wherein said sense and antisense region are capable of forming a double stranded RNA region comprising said at least 20 consecutive nucleotides.

a 3' end region involved in transcription termination and polyadenylation;

regenerating a population of transgenic plant lines from said transgenic plant cell; and identifying a stress tolerant plant line within said population of transgenic plant lines.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA region which is functionally or structurally defined, may comprise additional DNA regions etc.

It will thus be clear that the minimum nucleotide sequence of the antisense or sense RNA region of about 20 nt of the ParG coding region may be comprised within a larger RNA molecule, varying in size from 20 nt to a length equal to the size of the target gene.

The mentioned antisense or sense nucleotide regions may thus be about from about 21 nt to about 5000 nt long, such as 21 nt, 40 nt, 50 nt, 100 nt, 200 nt, 300 nt, 500 nt, 1000 nt, 2000 nt or even about 5000 nt or larger in length.

Moreover, it is not required for the purpose of the invention that the nucleotide sequence of the used inhibitory ParG RNA molecule or the encoding region of the chimeric gene, is completely identical or complementary to the endogenous ParG gene the expression of which is targeted to be reduced in the plant cell. The longer the sequence, the less stringent the requirement for the overall sequence identity is. Thus, the sense or antisense regions may have an overall sequence identity of about 40% or 50% or 60% or 70% or 80% or 90% or 100% to the nucleotide sequence of the endogenous ParG gene or the complement thereof. However, as mentioned antisense or sense regions should comprise a nucleotide sequence of 20 consecutive nucleotides having about 100% sequence identity to the nucleotide sequence of the endogenous ParG gene. Preferably the stretch of about 100% sequence identity should be about 50, 75 or 100 nt.

For the purpose of this invention, the "sequence identity" of two related nucleotide sequences, expressed as a percentage, refers to the number of positions in the two optimally aligned sequences which have identical residues (×100) divided by the number of positions compared. A gap, i.e. a position in an alignment where a residue is present in one sequence but not in the other is regarded as a position with non-identical residues. The alignment of the two sequences is performed by the Needleman and Wunsch algorithm (Needleman and Wunsch 1970) Computer-assisted sequence alignment, can be conveniently performed using standard software program such as GAP which is part of the Wisconsin Package Version 10.1 (Genetics Computer Group, Madison, Wis., USA) using the default scoring matrix with a gap creation penalty of 50 and a gap extension penalty of 3.

It will be clear that whenever nucleotide sequences of RNA molecules are defined by reference to nucleotide sequence of corresponding DNA molecules, the thymine (T) in the nucleotide sequence should be replaced by uracil (U). Whether reference is made to RNA or DNA molecules will be clear from the context of the application.

It will also be clear that chimeric genes capable of producing inhibitory ParG genes for a particular ParG gene in a particular plant variety or plant species, may also be used to inhibit ParG gene expression in other plant varieties or plant species. Indeed, when sufficient homology exists between the ParG inhibitory RNA region and the ParG gene, or when the ParG genes share the same stretch of 19 nucleotides, expression of those other genes will also be down-regulated.

In view of the potential role of ParG in nucleic acid metabolism, it may be advantageous that the expression of the endogenous ParG gene by the ParG inhibitory RNA is not completely inhibited. Downregulating the expression of a particular gene by gene silencing through the introduction of a chimeric gene encoding ParG inhibitory RNA will result in a population of different transgenic lines, exhibiting a distribution of different degrees of silencing of the ParG gene. The population will thus contain individual transgenic plant lines, wherein the endogenous ParG gene is silenced to the required degree of silencing. A person skilled in the art can easily identify such plant lines, e.g. by subjecting the plant lines to a particular adverse condition, such a high light intensity, oxidative stress, drought, heat etc. and selecting those plants which perform satisfactory and survive best the treatment.

As used herein, the term "promoter" denotes any DNA which is recognized and bound (directly or indirectly) by a DNA-dependent RNA-polymerase during initiation of transcription. A promoter includes the transcription initiation site, and binding sites for transcription initiation factors and RNA polymerase, and can comprise various other sites (e.g., enhancers), at which gene expression regulatory proteins may bind.

The term "regulatory region", as used herein, means any DNA, that is involved in driving transcription and controlling (i.e., regulating) the timing and level of transcription of a given DNA sequence, such as a DNA coding for a protein or polypeptide. For example, a 5' regulatory region (or "promoter region") is a DNA sequence located upstream (i.e., 5') of a coding sequence and which comprises the promoter and the 5'-untranslated leader sequence. A 3' regulatory region is a DNA sequence located downstream (i.e., 3') of the coding sequence and which comprises suitable transcription termination (and/or regulation) signals, including one or more polyadenylation signals.

In one embodiment of the invention the promoter is a constitutive promoter. In another embodiment of the invention, the promoter activity is enhanced by external or internal stimuli (inducible promoter), such as but not limited to hormones, chemical compounds, mechanical impulses, abiotic or biotic stress conditions. The activity of the promoter may also regulated in a temporal or spatial manner (tissue-specific promoters; developmentally regulated promoters).

For the purpose of the invention, the promoter is a plant-expressible promoter. As used herein, the term "plant-expressible promoter" means a DNA sequence which is capable of controlling (initiating) transcription in a plant cell. This includes any promoter of plant origin, but also any promoter of non-plant origin which is capable of directing transcription in a plant cell, i.e., certain promoters of viral or bacterial origin such as the CaMV35S (Hapster et al., 1988), the subterranean clover virus promoter No 4 or No 7 (WO9606932), or T-DNA gene promoters but also tissue-specific or organ-specific promoters including but not limited to seed-specific promoters (e.g., WO89/03887), organ-primordia specific promoters (An et al., 1996), stem-specific promoters (Keller et al., 1988), leaf specific promoters (Hudspeth et al., 1989), mesophyl-specific promoters (such as the light-inducible Rubisco promoters), root-specific promoters (Keller et al., 1989), tuber-specific promoters (Keil et al., 1989), vascular tissue specific promoters (Peleman et al., 1989), stamen-selective promoters (WO 89/10396, WO 92/13956), dehiscence zone specific promoters (WO 97/13865) and the like.

Methods for the introduction of chimeric genes into plants are well known in the art and include *Agrobacterium*-mediated transformation, particle gun delivery, microinjection, electroporation of intact cells, polyethyleneglycol-mediated protoplast transformation, electroporation of protoplasts, liposome-mediated transformation, silicon-whiskers mediated transformation etc. The transformed cells obtained in this way may then be regenerated into mature fertile plants.

The transgenic plant cells and plant lines according to the invention may further comprise chimeric genes which will reduce the expression of PARP genes as described in WO 00/04173. These further chimeric genes may be introduced e.g. by crossing the transgenic plant lines of the current invention with transgenic plants containing PARP gene expression reducing chimeric genes. Transgenic plant cells or plant lines may also be obtained by introducing or transforming the chimeric genes of the invention into transgenic plant cells comprising the PARP gene expression reducing chimeric genes or vice versa. Alternatively, the PARP and PARG inhibitory RNA regions may be encoded by one chimeric gene and transcribed as one RNA molecule.

The chimeric genes of the invention (or the inhibitory RNA molecules corresponding thereto) may also be introduced into plant cells in a transient manner, e.g. using the viral vectors, such as viral RNA vectors as described in WO 00/63397 or WO 02/13964.

Having read this specification, it will be immediately clear to the skilled artisan, that mutant plant cells and plant lines, wherein the PARG activity is reduced may be used to the same effect as the transgenic plant cells and plant lines described herein. Mutants in ParG gene of a plant cell or plant may be easily identified using screening methods known in the art, whereby chemical mutagenesis, such as e.g., EMS mutagenesis, is combined with sensitive detection methods (such as e.g., denaturing HPLC). An example of such a technique is the so-called "Targeted Induced Local Lesions in Genomes" method as described in McCallum et al, Plant Physiology 123 439-442 or WO 01/75167. However, other methods to detect mutations in particular genome regions or even alleles, are also available and include screening of libraries of existing or newly generated insertion mutant plant lines, whereby pools of genomic DNA of these mutant plant lines are subjected to PCR amplification using primers specific for the inserted DNA fragment and primers specific for the genomic region or allele, wherein the insertion is expected (see e.g. Maes et al., 1999, Trends in Plant Science, 4, pp 90-96).

Plant cell lines and plant lines may also be subjected to mutagenesis by selection for resistance to ParG inhibitors, such as gallotannines. (Ying, et al. (2001). Proc. Natl. Acad. Sci. USA 98(21), 12227-12232; Ying, W., Swanson, R. A. (2000). NeuroReport 11 (7), 1385-1388.

Thus, methods are available in the art to identify plant cells and plant lines comprising a mutation in the ParG gene. This population of mutant cells or plant lines can then be subjected to different abiotic stresses, and their phenotype or survival can be easily determined. Additionally, the NAD and/or the ATP content of the stressed cells can be determined and compared to results of such determinations of unstressed cells. In stress tolerant cells, the reduction of NAD content under stress conditions should when compared with unstressed cells, should be lower than for corresponding control cells.

It is also an object of the invention to provide plant cells and plants containing the chimeric genes or the RNA molecules according to the invention. Gametes, seeds, embryos, either zygotic or somatic, progeny or hybrids of plants comprising the chimeric genes of the present invention, which are produced by traditional breeding methods are also included within the scope of the present invention.

The plants obtained by the methods described herein may be further crossed by traditional breeding techniques with other plants to obtain stress tolerant progeny plants comprising the chimeric genes of the present invention.

The methods and means described herein are believed to be suitable for all plant cells and plants, both dicotyledonous and monocotyledonous plant cells and plants including but not limited to cotton, *Brassica* vegetables, oilseed rape, wheat, corn or maize, barley, alfalfa, peanuts, sunflowers, rice, oats, sugarcane, soybean, turf grasses, barley, rye, sorghum, sugar cane, vegetables (including chicory, lettuce, tomato, zucchini, bell pepper, eggplant, cucumber, melon, onion, leek), tobacco, potato, sugarbeet, papaya, pineapple, mango, *Arabidopsis thaliana*, but also plants used in horticulture, floriculture or forestry (poplar, fir, eucalyptus etc.).

The following non-limiting Examples describe method and means for increasing stress tolerance in plants according to the invention.

Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

Throughout the description and Examples, reference is made to the following sequences:

SEQ ID NO 1: amino acid sequence of the ParG protein from *Arabidopsis thaliana*.

SEQ ID NO 2: amino acid sequence of part of the ParG protein from *Solanum tuberosum*.

SEQ ID NO 3: nucleotide sequence encoding the ParG protein from *Arabidopsis thaliana*.

SEQ ID NO 4: nucleotide sequence encoding the part of the ParG protein from *Solanum tuberosum*.

SEQ ID NO 5: nucleotide sequence of an oligonucleotide primer suitable for PCR amplification of part of a ParG protein encoding DNA fragment.

SEQ ID NO 6: nucleotide sequence of an oligonucleotide primer suitable for PCR amplification of part of a ParG protein encoding DNA fragment.

SEQ ID NO 7: nucleotide sequence of an oligonucleotide primer suitable for PCR amplification of part of a ParG protein encoding DNA fragment.

SEQ ID NO 8: nucleotide sequence of an oligonucleotide primer suitable for PCR amplification of part of a ParG protein encoding DNA fragment.

SEQ ID NO 9: nucleotide sequence of the T-DNA vector containing the ParG expression reducing chimeric gene based on the *Arabidopsis* ParG gene sequence.

SEQ ID NO 10: amino acid sequence of conserved sequence 1 of PARG proteins.

SEQ ID NO 11: amino acid sequence of conserved sequence 2 of PARG proteins.

SEQ ID NO 12: amino acid sequence of conserved sequence 3 of PARG proteins.

SEQ ID NO 13: amino acid sequence of conserved sequence 4 of PARG proteins.

SEQ ID NO 14: amino acid sequence of conserved sequence 5 of PARG proteins.

SEQ ID NO 15: nucleotide sequence of the ParG protein from *Oryza sativa*.

SEQ ID NO 16: amino acid sequence of the ParG protein from *Oryza sativa*.

SEQ ID NO 17: nucleotide sequence of an oligonucleotide primer PG1 suitable for PCR amplification of part of a ParG protein encoding DNA fragment.

SEQ ID NO 18: nucleotide sequence of an oligonucleotide primer PG2 suitable for PCR amplification of part of a ParG protein encoding DNA fragment.

SEQ ID NO 19: nucleotide sequence of an oligonucleotide primer PG3 suitable for PCR amplification of part of a ParG protein encoding DNA fragment.

SEQ ID NO 20: nucleotide sequence of an oligonucleotide primer PG4 suitable for PCR amplification of part of a ParG protein encoding DNA fragment.

SEQ ID NO 21: nucleotide sequence of an oligonucleotide primer PG5 suitable for PCR amplification of part of a ParG protein encoding DNA fragment.

SEQ ID NO 22: nucleotide sequence of an oligonucleotide primer PG6 suitable for PCR amplification of part of a ParG protein encoding DNA fragment.

SEQ ID NO 23: nucleotide sequence encoding a ParG protein from *Zea mays*.

SEQ ID NO 24: nucleotide sequence of a T-DNA vector comprising a chimeric gene capable of reducing PARG expression.

SEQ ID NO 25: nucleotide sequence of a T-DNA vector comprising a chimeric gene capable of reducing PARG expression.

EXAMPLES

Example 1

Analysis of the Influence of Stress on Energy Production Efficiency of Transgenic Stress Tolerant Plant Lines Containing PARP Gene Expresssion Reducing Chimeric Genes Hypocotyls of transgenic *Brassica napus* plants comprising PARP gene expression reducing chimeric genes as described in WO 00/04173 were cultivated for 5 days on a growth medium. Explants were then transferred to liquid medium comprising 30 mg/L aspirin or acetylsalicylic acid (resulting in oxidative stress conditions) for one day. In control experiments, hypocotyls of non-transgenic *Brassica napus* plants N90-740 were cultivated on the same growth medium and then incubated for one day in liquid medium comprising 30 mg/L aspirin. In addition, hypocotyls of both the transgenic lines and the control line were cultivated on the same growth medium without aspirin.

After the cultivation period, the ATP content of 125 explants was determined for each experiment. Additionally, the oxygen consumed in 3 hours by 125 explants was determined. The results are summarized in Table 1. The standard error of the mean was less than 6%. Whereas, the ratio of moles ATP per mg consumed oxygen in the control plants decreased in the control plants when oxidative stress was applied, the same ratio in the stress tolerant transgenic plant lines actually increased under stress conditions, and was considerably higher (about 24%) than in the control plants. The stress resistant transgenic lines thus maintained an constant energy production efficiency, whereas the control lines exhibited an decreased energy production efficiency. In addition, superoxide production, expressed as a percentage of superoxide production in control plants not subjected to the oxidative stress, did not increase in stress tolerant plants subjected to stress conditions.

TABLE 1

Influence of stress on energy production efficiency of 5 days cultured *Brassica napus* hypocotyl explants.

| Plant line | Stress | moles ATP per 125 explants | $O_2$ mg/L consumed in 3 hrs by 125 explants | moles ATP mg consumed $O_2$ | Superoxide production |
|---|---|---|---|---|---|
| N90-740 (control) | None | $12.4 \times 10^{-7}$ | 2.96 | $4.19 \times 10^{-7}$ | 100% |
| | 30 mg/L aspirin | $13.2 \times 10^{-7}$ | 4.06 | $3.25 \times 10^{-7}$ | 167% |
| Transgenic line | None | $9.3 \times 10^{-7}$ | 2.33 | $3.99 \times 10^{-7}$ | 108% |
| | 30 mg/L aspirin | $11.4 \times 10^{-7}$ | 2.82 | $4.04 \times 10^{-7}$ | 100% |

Figure 2:
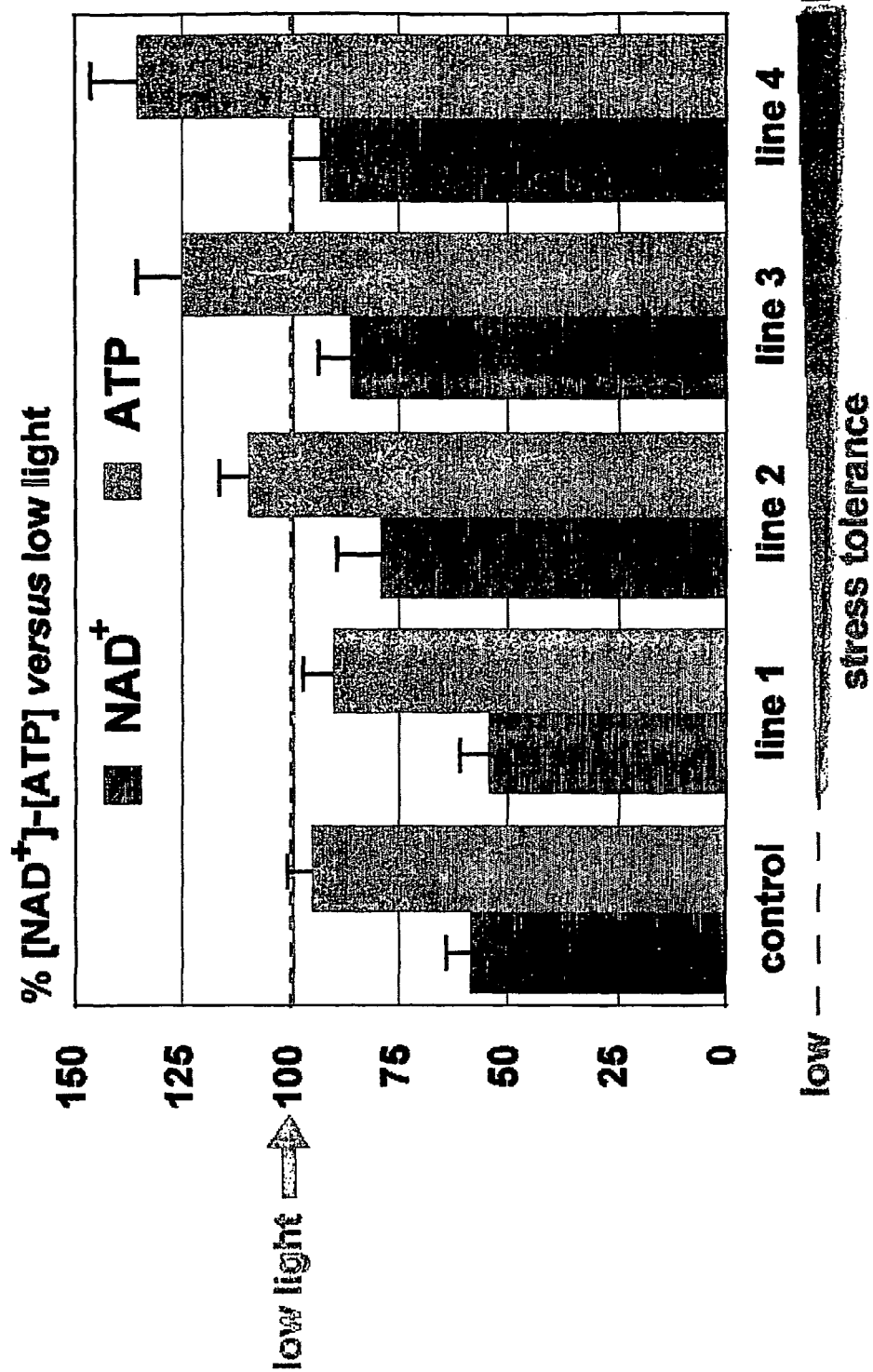
FIG. 2. Diagram of the NAD+ and ATP content of *Arabidopsis* lines under high light stress. Dark boxes represent NAD content under high light conditions expressed as percentage of the value for NAD content determined under low light conditions. Light boxes represent ATP content under high light conditions expressed as percentage of the value for ATP content determined under low light conditions.

In another experiment, the NAD+ and ATP content of 4 different transgenic *Arabidopsis* lines comprising PARP gene expression reducing chimeric genes as described in WO 00/04173 were determined under high and low light conditions, and compared to the values obtained for a non transformed control line under the same conditions. The 4 different lines exhibited different degrees of stress resistance as exhibited e.g. by their ability to withstand heat and/or drought conditions. The values obtained for the NAD and ATP contents under high light stress are expressed as a percentage of the values for the NAD and ATP contents under low light conditions, and are plotted in FIG. 2.

The results show that high light stress leads to a significant NAD reduction in control plant cells and in the transgenic plant line which is the least stress resistant. The more stress resistant the transgenic plant lines are, the less signicifant the NAD reduction is under high light stress conditions.

In another experiment, the NAD+ and ATP content of a segregating population resulting from a cross between transgenic corn lines comprising PARP gene expression reducing chimeric genes as described in WO 00/04173 and an untransformed corn line, were determined under conditions of nutrient (nitrogen) depletion, and compared to the values obtained for a non transformed control line under the same conditions.

Figure 3:
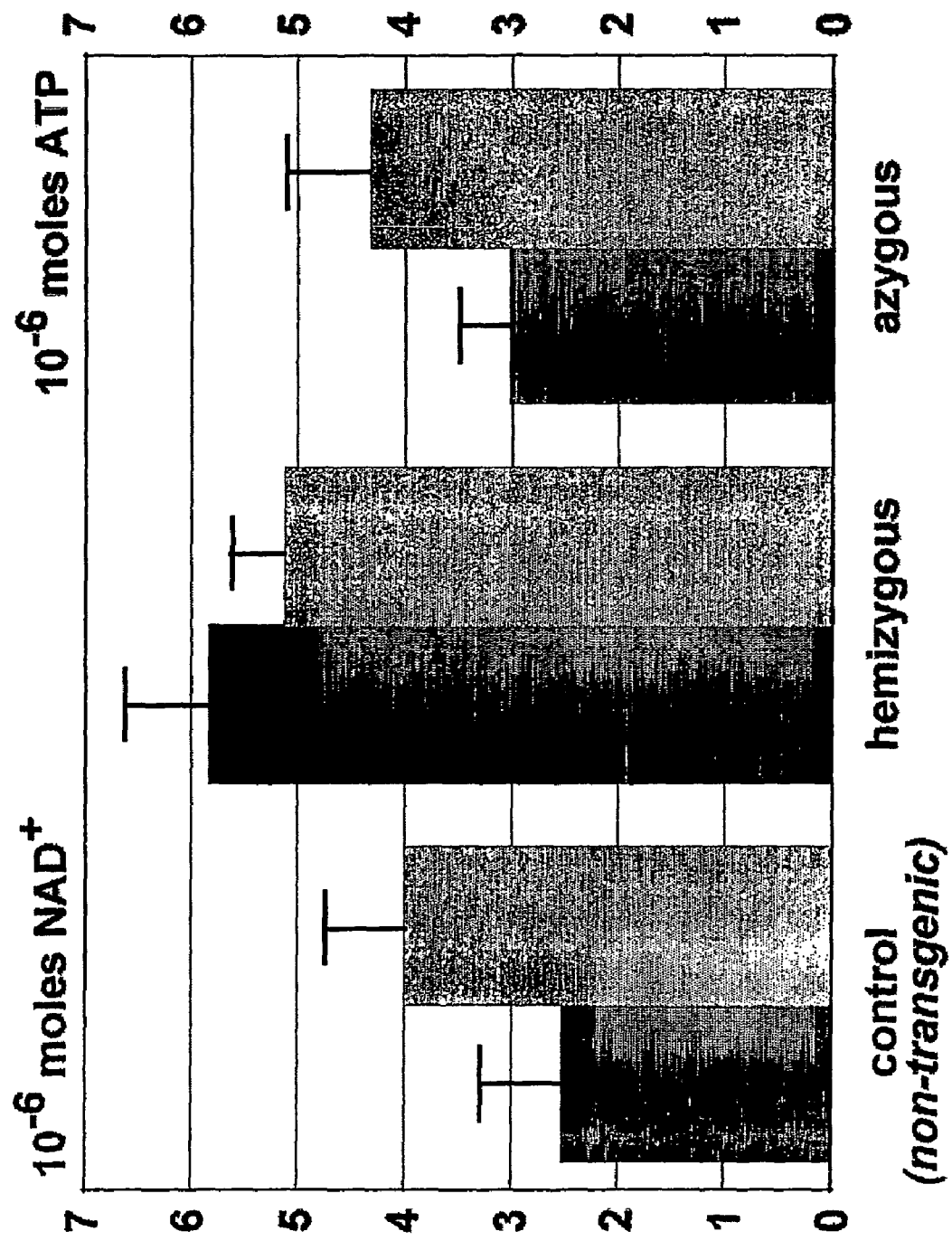
FIG. 3. Diagram of the NAD+ and ATP content of corn lines under nitrogen depletion stress. Dark boxes represent NAD content while light boxes represent ATP content.

FIG. 3 is a graphic representation of the of the obtained results. Hemizygous and azygous lines were discriminated by verification for the presence of the selectable marker gene. The NAD and ATP content was significantly higher in the hemizygous, stress tolerant plants than in the untransformed control plants or the azygous plants.

Example 2

Construction of ParG Gene Expression Reducing Chimeric Genes

To reduce the expression of the PARG gene e.g. in *Arabidopsis* and related plants, a chimeric gene was constructed which is capable expressing a dsRNA comprising both a sense and antisense region which can form a double stranded RNA. Such dsRNA is very effective in reducing the expression of the genes with which is shares sequence homology, by post-transcriptional silencing. The chimeric gene comprises the following DNA fragments:

A promoter region from Cauliflower mosaic Virus (CaMV 35S);

A DNA fragment comprising 163 bp from the ParG gene from *Arabidopsis thaliana* in direct orientation (Genbank Accession number AF394690 from nucleotide position 973 to 1135);

A DNA fragment encoding intron 2 from the pdk gene from Flaveria;

The DNA fragment comprising 163 bp from the ParG gene from *Arabidopsis thaliana* in inverted orientation (Genbank Accession number AF394690 from nucleotide position 973 to 1135);

A fragment of the 3' untranslated end from the octopine synthetase gene from *Agrobacterium tumefaciens*.

This chimeric gene was introduced in a T-DNA vector, between the left and right border sequences from the T-DNA, together with a selectable marker gene providing resistance to the herbicide phosphinotricin.

To reduce the expression of the PARG gene e.g. in potatoes and related plants, a chimeric gene is constructed which is capable expressing a dsRNA comprising both a sense and antisense region of a cDNA sequence from potato, that is capable of encoding a protein having high sequence identity with the N-terminal part of the *Arabidopsis* PARG protein. The chimeric gene comprises the following DNA fragments:

A promoter region from Cauliflower mosaic Virus (CaMV 35S);

A DNA fragment comprising a sequence of at least 100 bp from ParG homologue from *Solanum tuberosum* in direct orientation (Genbank Accession number BE340510);

A DNA fragment encoding intron 2 from the pdk gene from Flaveria;

The DNA fragment comprising the sequence of at least 100 bp from ParG homologue from *Solanum tuberosum* in inverted orientation (Genbank Accession number BE340510);

A fragment of the 3' untranslated end from the octopine synthetase gene from *Agrobacterium tumefaciens*.

This chimeric gene is introduced in a T-DNA vector, between the left and right border sequences from the T-DNA, together with a selectable marker gene providing resistance to the herbicide phosphinotricin.

Example 3

Analysis of Transgenic Plant Lines Comprising ParG Gene Expression Reducing Chimeric Genes The chimeric genes of Example 2 are introduced into *Arabidopsis* or potato respectively, by *Agrobacterium* mediated transformation.

The population of obtained transgenic lines is subjected to the following stress conditions, together with control plants:
   Increased heat for a period of days (greenhouse) or hours (in vitro)
   Drought for a period of days
   High light conditions for a period of days
   Nutrient depletion
   Individual plant lines surviving well the above mentioned stress conditions are selected.

The NAD content and ATP content for the above mentioned plants is determined under control and stress conditions.

Example 4

Quantitative Determination of NAD, ATP and Superoxide Radicals in Plant Cells

Quantification of ATP in plant tissues was done basically as decribed by Rawyler et al. (1999), Plant Physiol. 120, 293-300. The assay was used for the determination of the ATP content of hypocotyl explants that were cultured for 4-5 days on A2S3 medium or 2 weeks old in vitro cultured *Arabidopsis* plants. All manipulations are performed on crushed ice unless otherwhise indicated.

ATP Extraction
Freeze plant material with liquid nitrogen
   100 hypocotyl explants
   ±700 mg *Arabidopsis* plants (roots+shoots) (about 32-37 18-days old C24 plants)
Put frozen hypocotyls in mortar and add 6 ml of 6% perchloric acid.
Extraction can be done at room temperature using a pestle. After extraction, put samples as soon as possible on ice.
Centrifuge at 24,000 g (Sorvall, SS34 rotor at 14,000 rpm) for 10 min. at 4° C.
The supernatant is neutralized with 5M $K_2CO_3$ (add 350 µl of 5M $K_2CO_3$ to 3 ml of supernatant).
$KClO_4$ is removed by spinning as described above.
Quantitative bioluminescent determination of ATP
The ATP bioluminescent assay kit from Sigma is used (FL-M).
Dilute extract 6000×(about 6 mL extract from which 100 µl is taken, that is diluted 1000 times) The dilutions are made with the 'ATP assay mix dilution buffer' (FL-AAB) of the ATP bioluminescent assay kit
The amount of light that is produced is measured with the TD-20/20 luminometer of Turner Designs (Sunnyvale, USA).
Standard curve: disolve ATP standard of kit (FL-AAS) in 10 ml of water ($2\times10^{-6}$ moles)

Quantification of NAD+ and NADH in plant tissues was performed, essentially as described by Karp et al. (1983) or Filipovic et al. (1999) on the following plant material:

*Brassica napus:* 150 5-days cultured hypocotyl explants/sample *Arabidopsis:* 1000 mg 18-days old in vitro grown plants (shoots+roots)/sample (corresponds to ±60 C24 plants)

Assay Solution (A) For measuring NADH: 25 mM potassium phosphate buffer pH7
- 0.1 mM DTT
- 3 µM FMN (Fluka, 83810)
- 30 µM n-decanal (Sigma, D-7384)

(B) For measuring $NAD^+$+NADH:
- idem as for measuring NADH alone +2 µg/mL alcohol dehydrogenase (Roche, 102 717)

Extraction

Freeze with liquid nitrogen

Put frozen plant material in cooled mortar (cooled at −20° C.) and add 5 mL extraction buffer Grind material using a pestle Centrifuge at 24 000 g (Sorvall, SS34 rotor at 14 000 rpm) for 15 minutes at 4° C.

Take 1 mL of supernatant for analysis

Assay

NADH
- 390 µL of assay solution A
- +10 µL extract
- +2 µL NAD(P)H:FMN oxidoreductase
- +100 µL luciferase solution $NAD^+$+NADH
- 390 µL of assay solution B
- +10 µL extract
- 2 minutes at room temperature
- +2 µL NAD(P)H:FMN oxidoreductase
- +100 µL luciferase solution The amount of light that is produced is measured with the TD-20/20 luminometer of Turner Designs (Sunnyvale, USA)

NADH-Standard
- NADH stock solution: 1 mM (7.1 mg/10 mL $H_2O$) NADH: disodium salt, Roche, 107 735
- Dilution series in 10 mM potassium phosphate buffer pH7: $(10^{-2})$; $5 \times 10^{-3}$; $2 \times 10^{-3}$; $10^{-3}$; $5 \times 10^{-4}$
- Add 10 µL of dilutions in 390 µL of assay solution A and perform reaction
- Make standard curve Superoxide radicals production was measured by quantifying the reduction of XTT as described in De Block and De Brouwer (2002) Plant Physiol. Biochem. 40, 845-852

*Brassica Napus*

Media and reaction buffers

Sowing medium (medium 201):
- Half concentrated Murashige and Skoog salts
- 2% sucrose
- pH 5.8
- 0.6% agar (Difco Bacto Agar)
- 250 mg/l triacillin Callus inducing medium A2S3:
- MS medium, 0.5 g/l Mes (pH 5.8), 3% sucrose, 40 mg/l adenine-$SO_4$, 0.5% agarose, 1 mg/l 2,4-D, 0.25 mg/l NAA, 1 mg/l BAP, 250 mg/l triacillin Incubation medium:
- 25 mM K-phosphate buffer pH5.8
- 2% sucrose
- 1 drop Tween20 for 25 ml medium Reaction buffer:
- 50 mM K-phosphate buffer pH7.4
- 1 mM sodium,3'-{1-[phenylamino-carbonyl]-3,4-tetrazolium}-bis(4-methoxy-6-nitro)=XTT (bts, Germany, cat No. 2525)
- 1 drop Tween20 for 25 ml buffer Sterilization of seeds—pregermination of seeds—growing of the seedlings. Seeds are soaked in 70% ethanol for 2 min, then surface-sterilized for 15 min in a sodium hypochlorite solution (with about 6% active chlorine) containing 0.1% Tween20. Finally, the seeds are rinsed with 1l of sterile tap water. Incubate seeds for at least one hour in sterile tap water (to allow diffusion from seeds of components that may inhibit germination). Seeds are put in 250 ml erlenmeyer flasks containing 50 ml of sterile tap water (+250 mg/l triacillin). Shake for about 20 hours. Seeds from which the radicle is protruded are put in Vitro Vent containers from Duchefa containing about 125 ml of sowing medium (10 seeds/vessel, not too many to reduce loss of seed by contamination). The seeds are germinated at ±24° C. and 10-30:Einstein/$s^{-1}m^{-2}$ with a daylength of 16 h.

Preculture of the hypocotyl explants and induction of stress 12-14 days after sowing, the hypocotyls are cut in about 7-10 mm segments.

The hypocotyl explants (25 hypocotyls/Optilux Petridish, Falcon S1005, Denmark) are cultured for 5 days on medium A2S3 at 25° C. (at 10-30: Einstein/$s^{-1}m^{-2}$).

XTT-Assay

Transfer 150 hypocotyl explants to a 50 ml Falcon tube.

Wash with reaction buffer (without XTT).

Add 20 mL reaction buffer+XTT.
(explants have to be submerged, but do not vacuum infiltrate)

Incubate in the dark at 26° C. for about 3 hours

Measure the absorption of the reaction medium at 470 nm

*Arabidopsis Thaliana*

Media and reaction buffers

Plant medium:
- Half concentrated Murashige and Skoog salts
- B5 vitamins
- 1.5% sucrose
- pH 5.8
- 0.7% Difco agar Incubation medium:
- 10 mM K-phosphate buffer pH5.8
- 2% sucrose
- 1 drop Tween20 for 25 ml medium Reaction buffer:
- 50 mM K-phosphate buffer pH7.4
- 1 mM sodium,3'-{1-[phenylamino-carbonyl]-3,4-tetrazolium}-bis(4-methoxy-6-nitro)=XTT (bts, Germany, cat No. 2525)
- 1 drop Tween20 for 25 ml buffer Arabidopsis Plants

*Arabidopsis* lines: control
lines to test

Sterilization of *Arabidopsis* seeds:
- 2 min. 70% ethanol
- 10 min. bleach (6% active chlorine)+1 drop Tween 20 for 20 ml solution
- wash 5 times with sterile tap water Pregermination of seeds:
- In 9 cm Optilux Petridishes (Falcon) containing 12 ml sterile tap water.
- Low light overnight to 24 hours.

Growing of *Arabidopsis* plants
    Seeds are sown in Intergrid Tissue Culture disks of Falcon (nr. 3025) containing ±125 ml of plant medium: 1 seed/grid.
    Plants are grown at 24° C.
        30 µEinstein s$^{-1}$m$^{-2}$
        16 hours light-8 hours dark
    for about 3 weeks (before bolting)
XTT-Assay
Control Condition (No Stress)
    Harvest shoots (roots included) from agar plates and put them directly in a 50 ml Falcon tube containing reaction buffer (without XTT)
Stressed Shoots
    Transfer shoots to 50 ml Falcon tubes containing reaction buffer (without XTT)
    Replace reaction buffer with buffer containing XTT (40 mL/tube)
    Shoots have to be submerged, but do not vacuum infiltrate
    Incubate in the dark at 26° C. for about 3 hours
    Measure the absorption of the reaction medium at 470 nm
    Quantification of respiration by measuring oxygen consumption using a Clark polarographic electrode was done in the following way:
    Plant Material
*Brassica napus*
    150-200* hypocotyl explants
    Cultured for 5 days at 25° C.
    (cfr. protocol vigour assay)
    *150 explants error<10%; 200 explants error<6%
*Arabidopsis*
    For C24±1000 mg* in vitro plants (shoots+roots) (corresponds with ~50 18-days old plants)
    Pregerminate seeds before sowing
    Grow for 18 days at 24° C.
    (cfr. protocol in vitro growth *Arabidopis*)
    * for error<8%
    Incubation Media
*Brassica napus*
    25 mM K-phosphate buffer pH5.8
    2% sucrose
    Tween20 (1 drop/25 ml)
*Arabidopsis*
    10 mM K-phosphate buffer pH5.8
    2% sucrose
    Tween20 (1 drop/25 ml)

Before use, aerate (saturate with oxygen) medium well by stirring for at least a few hours
    Assay
    Put explants in 100 ml glass bottle (Schott, Germany) filled with incubation medium. Put the same weight of shoots in each bottle (±700 mg)
    Fill bottle to overflowing and close tightly (avoid large air bubbles)
    Fill also a bottle with incubation medium that does not contain explants (blanco)
    Incubate at 24° C. at low light for: 3-4 hours (*Brassica napus*) 3 hours (*Arabidopsis*)
    Shake gently during incubation (to avoid oxygen depletion of medium around explants)
    Measure oxygen concentration (mg/l) of incubation media using an hand-held dissolved oxygen meter (Cyberscan DO 310; Eutech Instruments, Singapore)

mg/l consumed oxygen=[oxygen]blanco–[oxygen]sample.

Example 5

Analysis of Transgenic Plant Lines Comprising ParG Gene Expression Reducing Chimeric Genes The chimeric genes of Example 2 were introduced into *Arabidopsis* an *Nicotiana tabacum* c.v. Petit Havana SR1 by *Agrobacterium* mediated transformation.

Transgenic seeds were germinated on a medium containing MS salts/2; B5 vitamins; 1,5% sucrose; pH=5.8 and 0.7% Difco agar. Germinated seeds were subject to low light (photosynthetic photon flux of about 30 µmol m$^{-1}$ s$^{-1}$ for 14 to 18 days, after which the light intensity was increased about 6-fold (photosynthetic photon flux of about 190 µmol m$^{-1}$ s$^{-1}$). After 1 day, the NAD and NADH contents were determined using the enzymatic cycling method (Karp et al. (1983) Anal. Biochem. 128, pp 175-180). A portion of the seedlings were cultivated further under high light conditions for about 3 to about days, after which the damage was scored. Damage was visible as darkening of the young leaves and shoot tip, bleaching of older leaves and growth retardation. The results are summarized in Table 2 for *Arabidopsis* and in Table 3 for tobacco.

TABLE 2

Analysis of Arabidopsis (Columbia).

| | High light tolerance | NAD + NADH content in 1 gram of tissue (10$^{-3}$ µM) | % TTC-reducing capacity vs control |
|---|---|---|---|
| Non-transgenic control | S | 17.3 | 100 |
| Transgenic line 9 | R | 28.2 | ND |
| Transgenic line 10 | R | 31.7 | ND |
| Transgenic line 11 | ±R | 26.5 | ND |
| Transgenic line 12 | S | 19.4 | ND |
| Transgenic line 26 | R | 33.2 | 55 |
| Transgenic line 27 | S | 21.3 | 100 |
| Transgenic line 28 | ±R | 26.5 | 75 |
| Transgenic line 29 | S | 17.7 | 102 |
| Transgenic line 30 | R | 28.3 | 66 |

±R indicates that some dark pigmentation was observed.
ND: not determined

TABLE 3

Analysis of *Nicotiana tabacum* c.v. Petit Havana SR1.

| | High light tolerance | % TTC-reducing capacity vs control |
|---|---|---|
| Non-transgenic control | S | 100 |
| Transgenic line 1 | R/S | 88 |
| Transgenic line 2 | ±R | 79 |
| Transgenic line 3 | R | 53 |

±R indicates that some dark pigmentation was observed.
R/S indicates tha the resistance phenotype was not very clear.

There is a positive correlation between the resistance to high light stress in the transgenic plants and the NAD+NADH content of the cells. An inverse correlation can be seen between TTC reducing capacity and high light tolerance.

Example 6

Construction of ParG Gene Expression Reducing Chimeric Genes Suited for Use in Cereal Plants To reduce the expression of the PARG gene e.g. in cereals such as rice or corn (maize) and related plants, a chimeric gene is constructed which is capable expressing a dsRNA comprising both a sense and antisense region of nucleotide sequence from rice, that is capable of encoding a protein having high sequence identity with PARG protein encoding nucleotide sequences. The chimeric gene comprises the following DNA fragments:

A promoter region from Cauliflower mosaic Virus (CaMV 35S);
A DNA fragment comprising a sequence of at least 100 bp from ParG homologue from *Oryza saliva* (SEQ ID No 15) in direct orientation;
A DNA fragment encoding intron 2 from the pdk gene from Flaveria;
A DNA fragment comprising a sequence of at least 100 bp from ParG homologue from *Oryza saliva* (SEQ ID No 15) in inverted orientation;
A fragment of the 3' untranslated end from the octopine synthetase gene from *Agrobacterium tumefaciens*.

This chimeric gene is introduced in a T-DNA vector, between the left and right border sequences from the T-DNA, together with a selectable marker gene providing resistance to e.g. the herbicide phosphinotricin.

To reduce the expression of the PARG gene e.g. in cereals such as rice or corn (maize) and related plants, a chimeric gene is constructed which is capable expressing a dsRNA comprising both a sense and antisense region of nucleotide sequence from rice, that is capable of encoding a protein having high sequence identity with PARG protein encoding nucleotide sequences. The chimeric gene comprises the following DNA fragments:

A promoter region from Cauliflower mosaic Virus (CaMV 35S);
A DNA fragment comprising a sequence of at least 100 bp from ParG homologue from *Zea mays* (SEQ ID No 23) in direct orientation;
A DNA fragment encoding intron 2 from the pdk gene from Flaveria;
A DNA fragment comprising a sequence of at least 100 bp from ParG homologue from *Zea mays* (SEQ ID No 23) in inverted orientation;
A fragment of the 3' untranslated end from the octopine synthetase gene from *Agrobacterium tumefaciens*.

This chimeric gene is introduced in a T-DNA vector, between the left and right border sequences from the T-DNA, together with a selectable marker gene providing resistance to e.g. the herbicide phosphinotricin. The nucleotide sequence of two examples of such T-DNA vectors comprising two different chimeric gences as described in the previous paragraph is represented in SEQ ID Nos 24 and 25.

Example 7

Analysis of Transgenic Plant Lines Comprising ParG Gene Expression Reducing Chimeric Genes The chimeric genes of Example 6 are introduced into rice or corn respectively, by *Agrobacterium* mediated transformation.

The population of obtained transgenic lines is subjected to the following stress conditions, together with control plants:
Increased heat for a period of days (greenhouse) or hours (in vitro)
Drought for a period of days
High light conditions for a period of days
Nutrient depletion Individual plant lines surviving well the above mentioned stress conditions, or at least one thereof, are selected.

The NAD content and ATP content for the above mentioned plants is determined under control and stress conditions.

The invention claimed is:

1. A method of producing an *Arabidopsis, Brassica* or tobacco plant tolerant to high light stress conditions, comprising the steps of:
   (a) transforming plant cells from an *Arabidopsis, Brassica* or tobacco plant with a chimeric gene to create transgenic plant cells, said chimeric gene comprising in sequence the following operably linked DNA fragments:
   (i) a plant-expressible promoter;
   (ii) a DNA region, which when transcribed yields a ParG inhibitory RNA molecule, said ParG inhibitory RNA molecule comprising a sense nucleotide sequence of at least 163 consecutive nucleotides of a coding region comprising the nucleotide sequence of SEQ ID No: 3 from the nucleotide at position 973 to the nucleotide at position 1135 and said ParG inhibitory RNA molecule further comprising an antisense nucleotide sequence of at least 163 consecutive nucleotides of said coding region, wherein said sense and antisense nucleotide sequences are capable of forming a double stranded RNA region comprising said at least 163 consecutive nucleotides; and
   (iii) a 3' end region involved in transcription termination and polyadenylation;
   (b) regenerating a population of transgenic plant lines from said transgenic plant cells wherein said chimeric gene is transcribed to yield said ParG inhibitory RNA molecule; and
   (c) identifying a plant line within said population of transgenic plant lines, which is tolerant to high light stress conditions as compared to an *Arabidopsis, Brassica,* or tobacco plant that does not comprise said chimeric gene.

* * * * *

SEQUENCE LISTING

```
<160> NUMBER OF SEQ ID NOS: 25

<210> SEQ ID NO 1
<211> LENGTH: 548
<212> TYPE: PRT
<213> ORGANISM: Arabidopsis thaliana

<400> SEQUENCE: 1

Met Glu Asn Arg Glu Asp Leu Asn Ser Ile Leu Pro Tyr Leu Pro Leu
1               5                   10                  15

Val Ile Arg Ser Ser Ser Leu Tyr Trp Pro Pro Arg Val Val Glu Ala
            20                  25                  30

Leu Lys Ala Met Ser Glu Gly Pro Ser His Ser Gln Val Asp Ser Gly
        35                  40                  45

Glu Val Leu Arg Gln Ala Ile Phe Asp Met Arg Arg Ser Leu Ser Phe
    50                  55                  60

Ser Thr Leu Glu Pro Ser Ala Ser Asn Gly Tyr Ala Phe Leu Phe Asp
65                  70                  75                  80

Glu Leu Ile Asp Glu Lys Glu Ser Lys Arg Trp Phe Asp Glu Ile Ile
                85                  90                  95
```

```
Pro Ala Leu Ala Ser Leu Leu Gln Phe Pro Ser Leu Leu Glu Val
            100                 105                 110

His Phe Gln Asn Ala Asp Asn Ile Val Ser Gly Ile Lys Thr Gly Leu
            115                 120                 125

Arg Leu Leu Asn Ser Gln Gln Ala Gly Ile Val Phe Leu Ser Gln Glu
            130                 135                 140

Leu Ile Gly Ala Leu Leu Ala Cys Ser Phe Phe Cys Leu Phe Pro Asp
145                 150                 155                 160

Asp Asn Arg Gly Ala Lys His Leu Pro Val Ile Asn Phe Asp His Leu
                165                 170                 175

Phe Ala Ser Leu Tyr Ile Ser Tyr Ser Gln Ser Gln Glu Ser Lys Ile
                180                 185                 190

Arg Cys Ile Met His Tyr Phe Glu Arg Phe Cys Ser Cys Val Pro Ile
                195                 200                 205

Gly Ile Val Ser Phe Glu Arg Lys Ile Thr Ala Ala Pro Asp Ala Asp
        210                 215                 220

Phe Trp Ser Lys Ser Asp Val Ser Leu Cys Ala Phe Lys Val His Ser
225                 230                 235                 240

Phe Gly Leu Ile Glu Asp Gln Pro Asp Asn Ala Leu Glu Val Asp Phe
                245                 250                 255

Ala Asn Lys Tyr Leu Gly Gly Ser Leu Ser Arg Gly Cys Val Gln
            260                 265                 270

Glu Glu Ile Arg Phe Met Ile Asn Pro Glu Leu Ile Ala Gly Met Leu
            275                 280                 285

Phe Leu Pro Arg Met Asp Asp Asn Glu Ala Ile Glu Ile Val Gly Ala
            290                 295                 300

Glu Arg Phe Ser Cys Tyr Thr Gly Tyr Ala Ser Ser Phe Arg Phe Ala
305                 310                 315                 320

Gly Glu Tyr Ile Asp Lys Lys Ala Met Asp Pro Phe Lys Arg Arg Arg
                325                 330                 335

Thr Arg Ile Val Ala Ile Asp Ala Leu Cys Thr Pro Lys Met Arg His
                340                 345                 350

Phe Lys Asp Ile Cys Leu Leu Arg Glu Ile Asn Lys Ala Leu Cys Gly
            355                 360                 365

Phe Leu Asn Cys Ser Lys Ala Trp Glu His Gln Asn Ile Phe Met Asp
            370                 375                 380

Glu Gly Asp Asn Glu Ile Gln Leu Val Arg Asn Gly Arg Asp Ser Gly
385                 390                 395                 400

Leu Leu Arg Thr Glu Thr Thr Ala Ser His Arg Thr Pro Leu Asn Asp
                405                 410                 415

Val Glu Met Asn Arg Glu Lys Pro Ala Asn Asn Leu Ile Arg Asp Phe
                420                 425                 430

Tyr Val Glu Gly Val Asp Asn Glu Asp His Glu Asp Asp Gly Val Ala
                435                 440                 445

Thr Gly Asn Trp Gly Cys Gly Val Phe Gly Gly Asp Pro Glu Leu Lys
            450                 455                 460

Ala Thr Ile Gln Trp Leu Ala Ala Ser Gln Thr Arg Arg Pro Phe Ile
465                 470                 475                 480

Ser Tyr Tyr Thr Phe Gly Val Glu Ala Leu Arg Asn Leu Asp Gln Val
                485                 490                 495

Thr Lys Trp Ile Leu Ser His Lys Trp Thr Val Gly Asp Leu Trp Asn
            500                 505                 510
```

```
Met Met Leu Glu Tyr Ser Ala Gln Arg Leu Tyr Lys Gln Thr Ser Val
        515                 520                 525

Gly Phe Phe Ser Trp Leu Leu Pro Ser Leu Ala Thr Thr Asn Lys Ala
        530                 535                 540

Ile Gln Pro Pro
545

<210> SEQ ID NO 2
<211> LENGTH: 169
<212> TYPE: PRT
<213> ORGANISM: Solanum tuberosum

<400> SEQUENCE: 2

Met Glu Asn Arg Glu Asp Val Lys Ser Ile Leu Pro Phe Leu Pro Val
1               5                  10                  15

Cys Leu Arg Ser Ser Leu Phe Trp Pro Leu Val Val Glu Ala
                20                  25                  30

Leu Lys Ala Leu Ser Glu Gly Pro His Tyr Ser Asn Val Asn Ser Gly
            35                  40                  45

Gln Val Leu Phe Leu Ala Ile Ser Asp Ile Arg Asn Ser Leu Ser Leu
        50                  55                  60

Pro Asp Ser Ser Ile Ser Ser Ala Ser Asp Gly Phe Ser Leu Leu
65                  70                  75                  80

Phe Asp Asp Leu Ile Pro Arg Asp Glu Ala Val Lys Trp Phe Lys Glu
                85                  90                  95

Val Val Pro Lys Met Ala Asp Leu Leu Leu Arg Leu Pro Ser Leu Leu
            100                 105                 110

Glu Ala His Tyr Glu Lys Ala Asp Gly Gly Ile Val Lys Gly Val Asn
        115                 120                 125

Thr Gly Leu Arg Leu Leu Glu Ser Gln Gln Pro Gly Ile Val Phe Leu
130                 135                 140

Ser Gln Glu Leu Val Gly Ala Leu Leu Ala Cys Ser Phe Phe Cys Tyr
145                 150                 155                 160

Ser Leu Pro Met Ile Glu Val Ser Val
                165

<210> SEQ ID NO 3
<211> LENGTH: 1647
<212> TYPE: DNA
<213> ORGANISM: Arabidopsis thaliana

<400> SEQUENCE: 3
atggagaatc gcgaagatct taactcaatt cttccgtacc ttccacttgt aattcgttcg      60
tcgtcgctgt attggccgcc gcgtgtggtg gaggcgttaa aggcaatgtc tgaaggacca     120
tctcacagcc aagttgactc aggagaggtt ctacggcaag ctattttcga tatgagacga     180 tcctatctt tctctactct cgagccatct gcttctaatg ctacgcatt tctctttgac      240 gaattgattg atgagaaaga atcaaagaga tggttcgatg agattatccc agcattggcg     300
agcttacttc tacagtttcc atctctgtta gaagtgcatt ccaaaatgc tgataatatt      360 gttagtggaa tcaaaaccgg tcttcgtttg ttaaattccc aacaagctgg cattgttttc     420
ctcagccagg agttgattgg agctcttctt gcatgctctt ctttttgttt gtttccggat     480
gataatagag gtgcaaaaca ccttccagtc atcaactttg atcatttgtt tgcaagcctt     540
tatataagtt atagtcaaag tcaagaaagc aagataagat gtattatgca ttactttgaa     600
aggttttgct cctgcgtgcc tattggtatt gtttcatttg aacgcaagat taccgctgct     660
```

```
cctgatgctg atttctggag caagtctgac gtttctcttt gtgcatttaa ggttcactct    720
tttgggttaa ttgaagatca acctgacaat gctctcgaag tggactttgc aaacaagtat    780
ctcggaggtg gttccctaag tagagggtgc gtgcaggaag agatacgctt catgattaac    840
cctgaattaa tcgctggcat gcttttcttg cctcggatgg atgacaatga agctatagaa    900
atagttggtg cggaaagatt ttcatgttac acagggtatg catcttcgtt tcggtttgct    960
ggtgagtaca ttgacaaaaa ggcaatggat cctttcaaaa ggcgaagaac cagaattgtt   1020
gcaattgatg cattatgtac accgaagatg agacacttta agatatatg tcttttaagg    1080
gaaattaata aggcactatg tggcttttta aattgtagca aggcttggga gcaccagaat   1140
atattcatgg atgaaggaga taatgaaatt cagcttgtcc gaaacggcag agattctggt   1200
cttctgcgta cagaaactac tgcgtcacac cgaactccac taaatgatgt tgagatgaat   1260
agagaaaagc ctgctaacaa tcttatcaga gatttttatg tggaaggagt tgataacgag   1320
gatcatgaag atgatggtgt cgcgacaggg aattggggat gtggtgtttt tggaggagac   1380
ccagagctaa aggctacgat acaatggctt gctgcttccc agactcgaag accatttata   1440
tcatattaca cctttggagt agaggcactc cgaaaccctag atcaggtgac gaagtggatt   1500
cttcccata aatggactgt tggagatctg tggaacatga tgttagaata ttctgctcaa   1560
aggctctaca agcaaaccag tgttggcttc ttttcttggc tacttccatc tctagctacc   1620
accaacaaag ctatccagcc gccttga                                       1647

<210> SEQ ID NO 4
<211> LENGTH: 598
<212> TYPE: DNA
<213> ORGANISM: Solanum tuberosum

<400> SEQUENCE: 4
gcaatggaga atagagaaga cgtgaagtca atccttccct ttttgccggt gtgtctccga     60
tcatcttctc ttttctggcc gccgctagtt gttgaagcac tgaaagcccct ctctgaaggc    120
cctcattaca gcaatgttaa ctccggccaa gtcctcttcc tcgcaatctc cgacattcgg    180
aattcccttt cactacctga ttcttcaatt tcctcttctg cttcagacgg attttctctc    240
ttatttgatg atttaattcc tagggatgaa gctgttaaat ggttcaaaga agtggtgccg    300
aaaatggcgg atttgctatt gcggttgcct tccttattgg aggctcacta tgagaaggct    360
gatggtggaa ttgttaaagg agtcaacact ggtcttcgct tattggaatc acaacagcct    420
ggcattgttt tcctcagtca ggaattagtc ggtgctcttc ttgcatgttc cttcttttgc    480
tattccctac caatgataga ggtatctgta tgatcagtat gacgagaaat ttgaaaataa    540
attgaagtgc attcttcact attttgagag gattggctca ttgatacctg cgggctac      598

<210> SEQ ID NO 5
<211> LENGTH: 37
<212> TYPE: DNA
<213> ORGANISM: Artificial Sequence
<220> FEATURE:
<223> OTHER INFORMATION: oligonucleotide primer ParGAt1

<400> SEQUENCE: 5
ggatcccctg caggacaaaa aggcaatgga tccttttc                             37

<210> SEQ ID NO 6
<211> LENGTH: 39
<212> TYPE: DNA
```

```
<213> ORGANISM: Artificial Sequence
<220> FEATURE:
<223> OTHER INFORMATION: oligonucleotide primer ParGAt2

<400> SEQUENCE: 6
gcacgaattc gcggccgcgg tgctcccaag ccttgctac                    39

<210> SEQ ID NO 7
<211> LENGTH: 39
<212> TYPE: DNA
<213> ORGANISM: Artificial Sequence
<220> FEATURE:
<223> OTHER INFORMATION: oligonucleotide primer ParGSt1

<400> SEQUENCE: 7
ggatcccctg caggctcact atgagaaggc tgatggtgg                    39

<210> SEQ ID NO 8
<211> LENGTH: 43
<212> TYPE: DNA
<213> ORGANISM: Artificial Sequence
<220> FEATURE:
<223> OTHER INFORMATION: oligonucleotide primer ParGSt2

<400> SEQUENCE: 8
gcacgaattc gcggccgcgt catactgatc atacagatac ctc               43

<210> SEQ ID NO 9
<211> LENGTH: 13466
<212> TYPE: DNA
<213> ORGANISM: Artificial Sequence
<220> FEATURE:
<223> OTHER INFORMATION: nucleotide sequence of pTVE428
<220> FEATURE:
<221> NAME/KEY: misc_feature
<222> LOCATION: (198)..(222)
<223> OTHER INFORMATION: Right T-DNA border
<220> FEATURE:
<221> NAME/KEY: misc_feature
<222> LOCATION: (983)..(273)
<223> OTHER INFORMATION: 3' ocs (3' untranslated end of octopine
      synthase gene)
<220> FEATURE:
<221> NAME/KEY: misc_feature
<222> LOCATION: (995)..(1155)
<223> OTHER INFORMATION: part of poly (ADP-ribose) glycohydrolase
<220> FEATURE:
<221> NAME/KEY: misc_feature
<222> LOCATION: (1929)..(1188)
<223> OTHER INFORMATION: intron 2 from the Pdk gene of Flaveria
<220> FEATURE:
<221> NAME/KEY: misc_feature
<222> LOCATION: (2122)..(1962)
<223> OTHER INFORMATION: part of poly (ADP-ribose) glycohydrolase
<220> FEATURE:
<221> NAME/KEY: misc_feature
<222> LOCATION: (3476)..(2131)
<223> OTHER INFORMATION: 35S promoter region from Cauliflower Mosaic
      Virus
<220> FEATURE:
<221> NAME/KEY: misc_feature
<222> LOCATION: (3948)..(3737)
<223> OTHER INFORMATION: 3' untranslated end of gene 7 from
      Agrobacterium tumefaciens
<220> FEATURE:
<221> NAME/KEY: misc_feature
<222> LOCATION: (4521)..(3970)
<223> OTHER INFORMATION: bar coding region
<220> FEATURE:
<221> NAME/KEY: misc_feature
<222> LOCATION: (6247)..(4522)
<223> OTHER INFORMATION: PSSuAra promoter region
<220> FEATURE:
```

<221> NAME/KEY: misc_feature
<222> LOCATION: (6415)..(6439)
<223> OTHER INFORMATION: left border region of T-DNA of Agrobacterium
      tumefaciens

<400> SEQUENCE: 9

```
agattcgaag ctcggtcccg tgggtgttct gtcgtctcgt tgtacaacga aatccattcc      60
cattccgcgc tcaagatggc ttcccctcgg cagttcatca gggctaaatc aatctagccg     120
acttgtccgg tgaaatgggc tgcactccaa cagaaacaat caaacaaaca tacacagcga     180
cttattcaca cgcgacaaat tacaacggta tatatcctgc cagtactcgg ccgtcgaccg     240
cggtaccccg gaattaagct tgcatgcctg caggtcctgc tgagcctcga catgttgtcg     300
caaaattcgc cctggacccg cccaacgatt tgtcgtcact gtcaaggttt gacctgcact     360
tcatttgggg cccacataca ccaaaaaaat gctgcataat tctcggggca gcaagtcggt     420
tacccggccg ccgtgctgga ccgggttgaa tggtgcccgt aactttcggt agagcggacg     480
gccaatactc aacttcaagg aatctcaccc atgcgcgccg gcgggaacc ggagttccct      540 tcagtgaacg ttattagttc gccgctcggt gtgtcgtaga tactagcccc tggggccttt     600
tgaaatttga ataagattta tgtaatcagt cttttaggtt tgaccggttc tgccgctttt     660
tttaaaattg gatttgtaat aataaaacgc aattgtttgt tattgtggcg ctctatcata     720
gatgtcgcta taaacctatt cagcacaata tattgttttc attttaatat tgtacatata     780
agtagtaggg tacaatcagt aaattgaacg gagaatatta ttcataaaaa tacgatagta     840
acgggtgata tattcattag aatgaaccga accggcggt aaggatctga gctacacatg       900
ctcaggtttt ttacaacgtg cacaacagaa ttgaaagcaa atatcatgcg atcataggcg     960
tctcgcatat ctcattaaag caggactcta gagacaaaaa ggcaatggat cctttcaaaa    1020
ggcgaagaac cagaattgtt gcaattgatg cattatgtac accgaagatg agacactta     1080 aagatatatg tcttttaagg gaattaata aggcactatg tggcttttta aattgtagca     1140
aggcttggga gcaccatcga tttcgaaccc agcttcccaa ctgtaatcaa tccaaatgta    1200
agatcaatga taacacaatg acatgatcta tcatgttacc ttgtttattc atgttcgact    1260
aattcattta attaatagtc aatccattta gaagttaata aaactacaag tattatttag    1320
aaattaataa gaatgttgat tgaaaataat actatataaa atgatagatc ttgcgctttg    1380
ttatattagc attagattat gttttgttac attagattac tgtttctatt agtttgatat    1440
tatttgttac tttagcttgt tatttaatat tttgtttatt gataaattac aagcagattg    1500
gaatttctaa caaaatattt attaactttt aaactaaaat atttagtaat ggtatagata    1560
tttaattata taataaacta ttaatcataa aaaaatatta ttttaattta tttattctta    1620
tttttactat agtattttat cattgatatt taattcatca aaccagctag aattactatt    1680
atgattaaaa caaatattaa tgctagtata tcatcttaca tgttcgatca aattcattaa    1740
aaataatata cttactctca acttttatct tcttcgtctt acacatcact tgtcatattt    1800
ttttacatta ctatgttgtt tatgtaaaca atatatttat aaattatttt ttcacaatta    1860
taacaactat attattataa tcatactaat taacatcact taactatttt atactaaaag    1920 gaaaaagaa aataattatt tccttaccaa gctggggtac cggtgctccc aagccttgct      1980
acaatttaaa aagccacata gtgccttatt aattcccctt aaaagacata tatctttaaa    2040
gtgtctcatc ttcggtgtac ataatgcatc aattgcaaca attctggttc ttcgcctttt    2100
gaaaggatcc attgcctttt tgtcctcgag cgtgtcctct ccaaatgaaa tgaacttcct    2160
```

```
tatatagagg aagggtcttg cgaaggatag tgggattgtg cgtcatccct tacgtcagtg   2220
gagatgtcac atcaatccac ttgctttgaa gacgtggttg gaacgtcttc tttttccacg   2280
atgctcctcg tgggtggggg tccatctttg ggaccactgt cggcagagag atcttgaatg   2340
atagcctttc ctttatcgca atgatggcat ttgtaggagc caccttcctt ttctactgtc   2400
ctttcgatga agtgacagat agctgggcaa tggaatccga ggaggtttcc cgaaattatc   2460
ctttgttgaa aagtctcaat agcccttttgg tcttctgaga ctgtatcttt gacattttttg  2520
gagtagacca gagtgtcgtg ctccaccatg ttgacgaaga ttttcttctt gtcattgagt   2580
cgtaaaagac tctgtatgaa ctgttcgcca gtcttcacgg cgagttctgt tagatcctcg   2640
atttgaatct tagactccat gcatggcctt agattcagta ggaactacct ttttagagac   2700
tccaatctct attacttgcc ttggtttatg aagcaagcct tgaatcgtcc atactggaat   2760
agtacttctg atcttgagaa atatgtcttt ctctgtgttc ttgatgcaat tagtcctgaa   2820
tctttgact gcatctttaa ccttcttggg aaggtatttg atctcctgga gattgttact   2880
cgggtagatc gtcttgatga gacctgctgc gtaggcctct ctaaccatct gtgggtcagc   2940
attctttctg aaattgaaga ggctaacctt ctcattatca gtggtgaaca tagtgtcgtc   3000
accttcacct tcgaacttcc ttcctagatc gtaaagatag aggaaatcgt ccattgtaat   3060
ctccggggca aaggagatct cttttggggc tggatcactg ctgggccttt tggttcctag   3120
cgtgagccag tgggcttttt gctttggtgg gcttgttagg gccttagcaa agctcttggg   3180
cttgagttga gcttctcctt tggggatgaa gttcaacctg tctgtttgct gacttgttgt   3240
gtacgcgtca gctgctgctc ttgcctctgt aatagtggca aatttcttgt gtgcaactcc   3300
gggaacgccg tttgttgccg cctttgtaca accccagtca tcgtatatac cggcatgtgg   3360
accgttatac acaacgtagt agttgatatg agggtgttga atacccgatt ctgctctgag   3420
aggagcaact gtgctgttaa gctcagattt ttgtgggatt ggaattaatt cgtcgagcgg   3480
ccgctcgacg agcgcgccga tatcgcgatc gcccgggccg gccatttaaa tgaattcgag   3540
ctcggtaccc aaacgcggcc gcaagctata acttcgtata gcatacatta tacgaagtta   3600
ttcgactcta gaggatccca attcccatgc atggagtcaa agattcaaat agaggacact   3660
tctcgaactc ggccgtcgaa ctcggccgtc gagtacatgg tcgataagaa aaggcaattt   3720
gtagatgtta attcccatct tgaaagaaat atagtttaaa tatttattga taaaataaca   3780
agtcaggtat tatagtccaa gcaaaaacat aaatttattg atgcaagttt aaattcagaa   3840
atatttcaat aactgattat atcagctggt acattgccgt agatgaaaga ctgagtgcga   3900
tattatgtgt aatacataaa ttgatgatat agctagctta gctcatcggg ggatcctaga   3960
cgcgtgagat cagatctcgg tgacgggcag gaccggacgg ggcggtaccg gcaggctgaa   4020
gtccagctgc cagaaaccca cgtcatgcca gttcccgtgc ttgaagccgg ccgcccgcag   4080
catgccgcgg gggcatatcc gagcgcctc gtgcatgcgc acgctcgggt cgttgggcag   4140
cccgatgaca gcgaccacgc tcttgaagcc ctgtgcctcc agggacttca gcaggtgggt   4200
gtagagcgtg gagcccagtc ccgtccgctg gtggcggggg gagacgtaca cggtcgactc   4260
ggccgtccag tcgtaggcgt tgcgtgcctt ccagggccc gcgtaggcga tgccggcgac   4320
ctcgccgtcc acctcggcga cgagccaggg atagcgctcc cgcagacgga cgaggtcgtc   4380
cgtccactcc tgcggttcct gcggctcggt acggaagttg accgtgcttg tctcgatgta   4440
gtggttgacg atggtgcaga ccgccggcat gtccgcctcg gtggcacggc ggatgtcggc   4500
cgggcgtcgt tctgggtcca ttgttcttct ttactctttg tgtgactgag gtttggtcta   4560
```

```
gtgctttggt catctatata taatgataac aacaatgaga acaagctttg gagtgatcgg    4620
agggtctagg atacatgaga ttcaagtgga ctaggatcta caccgttgga tttttgagtgt   4680 ggatatgtgt gaggttaatt ttacttggta acggccacaa aggcctaagg agaggtgttg    4740
agacccttat cggcttgaac cgctggaata atgccacgtg gaagataatt ccatgaatct    4800
tatcgttatc tatgagtgaa attgtgtgat ggtggagtgg tgcttgctca ttttacttgc    4860
ctggtggact tggcccttttc cttatgggga atttatattt tacttactat agagctttca   4920
tacctttttt ttaccttgga tttagttaat atataatggt atgattcatg aataaaaatg    4980
ggaaattttt gaatttgtac tgctaaatgc ataagattag gtgaaactgt ggaatatata    5040 ttttttttcat ttaaaagcaa aatttgcctt ttactagaat tataaatata gaaaatata    5100 taacattcaa ataaaaatga aataagaac tttcaaaaaa cagaactatg tttaatgtgt     5160
aaagattagt cgcacatcaa gtcatctgtt acaatatgtt acaacaagtc ataagcccaa    5220
caaagttagc acgtctaaat aaactaaaga gtccacgaaa atattacaaa tcataagccc    5280
aacaaagtta ttgatcaaaa aaaaaaaacg cccaacaaag ctaaacaaag tccaaaaaaa    5340
acttctcaag tctccatctt cctttatgaa cattgaaaac tatacacaaa acaagtcaga    5400
taaatctctt tctgggcctg tcttcccaac ctcctacatc acttccctat cggattgaat    5460
gttttacttg taccttttcc gttgcaatga tattgatagt atgtttgtga aaactaatag    5520
ggttaacaat cgaagtcatg gaatatggat ttggtccaag atttccgag agctttctag     5580 tagaaagccc atcaccagaa atttactagt aaaataaatc accaattagg tttcttatta    5640
tgtgccaaat tcaatataat tatagaggat atttcaaatg aaaacgtatg aatgttatta    5700
gtaaatggtc aggtaagaca ttaaaaaaat cctacgtcag atattcaact ttaaaaattc    5760
gatcagtgtg gaattgtaca aaaatttggg atctactata tatatataat gctttacaac    5820
acttggattt ttttttggag gctggaattt ttaatctaca tatttgtttt ggccatgcac    5880
caactcattg tttagtgtaa tactttgatt ttgtcaaata tatgtgttcg tgtatatttg    5940
tataagaatt tctttgacca tatacacaca cacatatata tatatatata tatattatat    6000
atcatgcact tttaattgaa aaaataatat atatatatat agtgcatttt ttctaacaac    6060
catatatgtt gcgattgatc tgcaaaaata ctgctagagt aatgaaaaat ataatctatt    6120
gctgaaatta tctcagatgt taagattttc ttaaagtaaa ttctttcaaa ttttagctaa    6180
aagtcttgta ataactaaag aataatacac aatctcgacc acggaaaaaa aacacataat    6240
aaatttgaat ttcgaccgcg gtacccggaa ttgggttata attacctcag gtcgaggaat    6300
taattcggta cgtacctaat aacttcgtat agcatacatt tacgaagtt atatggatct     6360 cgaggcatta cggcattacg gcactcgcga gggtcccaat tcgagcatgg agccatttac    6420
aattgaatat atcctgccgc cgctgccgct ttgcacccgg tggagcttgc atgttggttt    6480
ctacgcagaa ctgagccggt taggcagata atttccattg agaactgagc catgtgcacc    6540
ttccccccaa cacggtgagc gacggggcaa cggagtgatc cacatgggac ttttaaacat    6600
catccgtcgg atggcgttgc gagagaagca gtcgatccgt gagatcagcc gacgcaccgg    6660
gcaggcgcgc aacacgatcg caaagtattt gaacgcaggt acaatcgagc cgacgttcac    6720
ggtaccggaa cgaccaagca agctagctta gtaaagccct cgctagattt taatgcggat    6780
gttgcgatta cttcgccaac tattgcgata acaagaaaaa gccagccttt catgatatat    6840
ctcccaattt gtgtagggct tattatgcac gcttaaaaat aataaaagca gacttgacct    6900
```

```
gatagtttgg ctgtgagcaa ttatgtgctt agtgcatcta acgcttgagt taagccgcgc   6960
cgcgaagcgg cgtcggcttg aacgaattgt tagacattat ttgccgacta ccttggtgat   7020
ctcgcctttc acgtagtgga caaattcttc caactgatct gcgcgcgagg ccaagcgatc   7080
ttcttcttgt ccaagataag cctgtctagc ttcaagtatg acgggctgat actgggccgg   7140
caggcgctcc attgcccagt cggcagcgac atccttcggc gcgattttgc cggttactgc   7200
gctgtaccaa atgcgggaca acgtaagcac tacatttcgc tcatcgccag cccagtcggg   7260
cggcgagttc catagcgtta aggtttcatt tagcgcctca aatagatcct gttcaggaac   7320
cggatcaaag agttcctccg ccgctggacc taccaaggca acgctatgtt ctcttgcttt   7380
tgtcagcaag atagccagat caatgtcgat cgtggctggc tcgaagatac ctgcaagaat   7440
gtcattgcgc tgccattctc caaattgcag ttcgcgctta gctggataac gccacggaat   7500
gatgtcgtcg tgcacaacaa tggtgacttc tacagcgcgg agaatctcgc tctctccagg   7560
ggaagccgaa gtttccaaaa ggtcgttgat caaagctcgc cgcgttgttt catcaagcct   7620
tacggtcacc gtaaccagca aatcaatatc actgtgtggc ttcaggccgc catccactgc   7680
ggagccgtac aaatgtacgg ccagcaacgt cggttcgaga tggcgctcga tgacgccaac   7740
tacctctgat agttgagtcg atacttcggc gatcaccgct tccctcatga tgtttaactt   7800
tgttttaggg cgactgccct gctgcgtaac atcgttgctg ctccataaca tcaaacatcg   7860
acccacggcg taacgcgctt gctgcttgga tgcccgaggc atagactgta ccccaaaaaa   7920
acagtcataa caagccatga aaaccgccac tgcgccgtta ccaccgctgc gttcggtcaa   7980
ggttctggac cagttgcgtg agcgcatacg ctacttgcat tacagcttac gaaccgaaca   8040
ggcttatgtc cactgggttc gtgccttcat ccgtttccac ggtgtgcgtc acccggcaac   8100
cttgggcagc agcgaagtcg aggcatttct gtcctggctg gcgaacgagc gcaaggtttc   8160
ggtctccacg catcgtcagg cattggcggc cttgctgttc ttctacggca agtgctgtgc   8220
acggatctgc cctggcttca ggagatcgga agacctcggc cgtccgggcg cttgccggtg   8280
gtgctgaccc cggatgaagt ctctagagct ctagagggtt cgcatcctcg gttttctgga   8340
aggcgagcat cgtttgttcg cccagcttct gtatggaacg ggcatgcgga tcagtgaggg   8400
tttgcaactg cgggtcaagg atctggattt cgatcacggc acgatcatcg tgcgggaggg   8460
caagggctcc aaggatcggg ccttgatgtt acccgagagc ttggcaccca gcctgcgcga   8520
gcagggatcg atccaacccc tccgctgcta tagtgcagtc ggcttctgac gttcagtgca   8580
gccgtcttct gaaaacgaca tgtcgcacaa gtcctaagtt acgcgacagg ctgccgccct   8640
gccctttttcc tggcgttttc ttgtcgcgtg ttttagtcgc ataaagtaga atacttgcga   8700
ctagaaccgg agacattacg ccatgaacaa gagcgccgcc gctggcctgc tgggctatgc   8760
ccgcgtcagc accgacgacc aggacttgac caaccaacgg gccgaactgc acgcggccgg   8820
ctgcaccaag ctgttttccg agaagatcac cggcaccagg cgcgaccgcc cggagctggc   8880
caggatgctt gaccacctac gccctggcga cgttgtgaca gtgaccaggc tagaccgcct   8940
ggcccgcagc acccgcgacc tactggacat tgccgagcgc atccaggagg ccggcgcggg   9000
cctgcgtagc ctggcagagc cgtgggccga caccaccacg ccggccggcc gcatggtgtt   9060
gaccgtgttc gccggcattg ccgagttcga gcgttcccta atcatcgacc gcacccggag   9120
cgggcgcgag gccgccaagg cccgaggcgt gaagtttggc cccgccccta ccctcacccc   9180
ggcacagatc gcgcacgccc gcgagctgat cgaccaggaa ggccgcaccg tgaaagaggc   9240
ggctgcactg cttggcgtgc atcgctcgac cctgtaccgc gcacttgagc gcagcgagga   9300
```

-continued

```
agtgacgccc accgaggcca ggcggcgcgg tgccttccgt gaggacgcat tgaccgaggc    9360
cgacgccctg gcggccgccg agaatgaacg ccaagaggaa caagcatgaa accgcaccag    9420
gacgccagg acgaaccgtt tttcattacc gaagagatcg aggcggagat gatcgcggcc    9480
gggtacgtgt tcgagccgcc cgcgcacgtc tcaaccgtgc ggctgcatga atcctggcc    9540
ggtttgtctg atgccaagct ggcggcctgg ccggccagct tggccgctga agaaaccgag    9600
cgccgccgtc taaaaggtg atgtgtattt gagtaaaaca gcttgcgtca tgcggtcgct    9660
gcgtatatga tgcgatgagt aaataaacaa atacgcaagg ggaacgcatg aaggttatcg    9720
ctgtacttaa ccagaaaggc gggtcaggca agacgaccat cgcaacccat ctagcccgcg    9780
ccctgcaact cgccggggcc gatgttctgt tagtcgattc cgatccccag ggcagtgccc    9840
gcgattgggc ggccgtgcgg gaagatcaac cgctaaccgt tgtcggcatc gaccgcccga    9900
cgattgaccg cgacgtgaag gccatcggcc ggcgcgactt cgtagtgatc gacggagcgc    9960
cccaggcggc ggacttggct gtgtccgcga tcaaggcagc cgacttcgtg ctgattccgg   10020
tgcagccaag cccttacgac atatgggcca ccgccgacct ggtggagctg gttaagcagc   10080
gcattgaggt cacggatgga aggctacaag cggcctttgt cgtgtcgcgg gcgatcaaag   10140
gcacgcgcat cggcggtgag gttgccgagg cgctggccgg gtacgagctg cccattcttg   10200
agtcccgtat cacgcagcgc gtgagctacc caggcactgc cgccgccggc acaaccgttc   10260
ttgaatcaga acccgagggc gacgctgccc gcgaggtcca ggcgctggcc gctgaaatta   10320
aatcaaaact catttgagtt aatgaggtaa agagaaaatg agcaaaagca caaacacgct   10380
aagtgccggc cgtccgagcg cacgcagcag caaggctgca acgttggcca gcctggcaga   10440
cacgccagcc atgaagcggg tcaactttca gttgccggcg gaggatcaca ccaagctgaa   10500
gatgtacgcg gtacgccaag gcaagaccat taccgagctg ctatctgaat acatcgcgca   10560
gctaccagag taaatgagca aatgaataaa tgagtagatg aattttagcg gctaaaggag   10620
gcggcatgga aaatcaagaa caaccaggca ccgacgccgt ggaatgcccc atgtgtggag   10680
gaacgggcg ttggccaggc gtaagcggct gggttgtctg ccggccctgc aatggcactg   10740
gaacccccaa gcccgaggaa tcggcgtgac ggtcgcaaac catccggccc ggtacaaatc   10800
ggcgcggcgc tgggtgatga cctggtggag aagttgaagg ccgcgcaggc cgcccagcgg   10860
caacgcatcg aggcagaagc acgccccggt gaatcgtggc aagcggccgc tgatcgaatc   10920
cgcaaagaat cccggcaacc gccggcagcc ggtgcgccgt cgattaggaa gccgcccaag   10980
ggcgacgagc aaccagattt tttcgttccg atgctctatg acgtgggcac ccgcgatagt   11040
cgcagcatca tggacgtggc cgttttccgt ctgtcgaagc gtgaccgacg agctggcgag   11100
gtgatccgct acgagcttcc agacgggcac gtagaggttt ccgcagggcc ggccggcatg   11160
gccagtgtgt gggattacga cctggtactg atggcggttt cccatctaac cgaatccatg   11220
aaccgatacc gggaagggaa gggagacaag cccggccgcg tgttccgtcc acacgttgcg   11280
gacgtactca agttctgccg gcgagccgat ggcggaaagc agaaagacga cctggtagaa   11340
acctgcattc ggttaaacac cacgcacgtt gccatgcagc gtacgaagaa ggccaagaac   11400
ggccgcctgg tgacggtatc cgagggtgaa gccttgatta gccgctacaa gatcgtaaag   11460
agcgaaaccg ggcggccgga gtacatcgag atcgagctag ctgattggat gtaccgcgag   11520
atcacagaag gcaagaaccc ggacgtgctg acggttcacc ccgattactt tttgatcgat   11580
cccggcatcg gccgttttct ctaccgcctg gcacgccgcg ccgcaggcaa ggcagaagcc   11640
```

-continued

```
agatggttgt tcaagacgat ctacgaacgc agtggcagcg ccggagagtt caagaagttc    11700
tgtttcaccg tgcgcaagct gatcgggtca aatgacctgc cggagtacga tttgaaggag    11760 gaggcgggc aggctggccc gatcctagtc atgcgctacc gcaacctgat cgagggcgaa    11820
gcatccgccg gttcctaatg tacggagcag atgctagggc aaattgccct agcaggggaa    11880
aaaggtcgaa aaggtctctt tcctgtggat agcacgtaca ttgggaaccc aaagccgtac    11940
attgggaacc ggaacccgta cattgggaac ccaaagccgt acattgggaa ccggtcacac    12000
atgtaagtga ctgatataaa agagaaaaaa ggcgattttt ccgcctaaaa ctctttaaaa    12060
cttattaaaa ctcttaaaac ccgcctggcc tgtgcataac tgtctggcca gcgcacagcc    12120
gaagagctgc aaaaagcgcc taccctttcgg tcgctgcgct ccctacgccc gccgcttcg    12180 cgtcggccta tcgcggccgc tggccgctca aaaatggctg gcctacgcc aggcaatcta    12240 ccagggcgcg acaagccgc gccgtcgcca ctcgaccgcc ggcgcccaca tcaaggcacc    12300
ctgcctcgcg cgtttcggtg atgacggtga aaacctctga cacatgcagc tcccggagac    12360
ggtcacagct tgtctgtaag cggatgccgg gagcagacaa gcccgtcagg gcgcgtcagc    12420
gggtgttggc gggtgtcggg gcgcagccat gacccagtca cgtagcgata gcggagtgta    12480
tactggctta actatgcggc atcagagcag attgtactga gagtgcacca tatgcggtgt    12540
gaaataccgc acagatgcgt aaggagaaaa taccgcatca ggcgctcttc cgcttcctcg    12600
ctcactgact cgctgcgctc ggtcgttcgg ctgcggcgag cggtatcagc tcactcaaag    12660
gcggtaatac ggttatccac agaatcaggg gataacgcag gaaagaacat gtgagcaaaa    12720
ggccagcaaa aggccaggaa ccgtaaaaag gccgcgttgc tggcgttttt ccataggctc    12780
cgcccccctg acgagcatca caaaaatcga cgctcaagtc agaggtggcg aaacccgaca    12840
ggactataaa gataccaggc gtttccccct ggaagctccc tcgtgcgctc tcctgttccg    12900
accctgccgc ttaccggata cctgtccgcc tttctccctt cgggaagcgt ggcgctttct    12960
catagctcac gctgtaggta tctcagttcg gtgtaggtcg ttcgctccaa gctgggctgt    13020
gtgcacgaac ccccgttca gcccgaccgc tgcgccttat ccggtaacta tcgtcttgag    13080
tccaacccgg taagacacga cttatcgcca ctggcagcag ccactggtaa caggattagc    13140
agagcgaggt atgtaggcgg tgctacagag ttcttgaagt ggtggcctaa ctacggctac    13200
actagaagga cagtatttgg tatctgcgct ctgctgaagc cagttacctt cggaaaaaga    13260
gttggtagct cttgatccgg caaacaaacc accgctggta gcggtggttt tttgtttgc    13320 aagcagcaga ttacgcgcag aaaaaaagga tctcaagaag atccgaaaaa cgcaagcgca    13380
aagagaaagc aggtagcttg cagtgggctt acatggcgat agctagactg ggcggtttta    13440
tggacagcaa gcgaaccgga attgcc                                         13466
```

```
<210> SEQ ID NO 10
<211> LENGTH: 31
<212> TYPE: PRT
<213> ORGANISM: Artificial Sequence
<220> FEATURE:
<223> OTHER INFORMATION: Consensus sequence 1 of PARG protein
<220> FEATURE:
<221> NAME/KEY: MISC_FEATURE
<222> LOCATION: (2)..(2)
<223> OTHER INFORMATION: X represents any amino acid
<220> FEATURE:
<221> NAME/KEY: MISC_FEATURE
<222> LOCATION: (8)..(10)
<223> OTHER INFORMATION: X represents any amino acid
<220> FEATURE:
<221> NAME/KEY: MISC_FEATURE
```

```
<222> LOCATION: (14)..(17)
<223> OTHER INFORMATION: X represents any amino acid
<220> FEATURE:
<221> NAME/KEY: MISC_FEATURE
<222> LOCATION: (19)..(19)
<223> OTHER INFORMATION: X represents any amino acid
<220> FEATURE:
<221> NAME/KEY: MISC_FEATURE
<222> LOCATION: (27)..(29)
<223> OTHER INFORMATION: X represents any amino acid

<400> SEQUENCE: 10

Leu Xaa Val Asp Phe Ala Asn Xaa Xaa Xaa Gly Gly Gly Xaa Xaa Xaa
1               5                   10                  15

Xaa Gly Xaa Val Gln Glu Glu Ile Arg Phe Xaa Xaa Xaa Pro Glu
            20                  25                  30

<210> SEQ ID NO 11
<211> LENGTH: 20
<212> TYPE: PRT
<213> ORGANISM: Artificial Sequence
<220> FEATURE:
<223> OTHER INFORMATION: Consensus sequence 2 for PARG protein
<220> FEATURE:
<221> NAME/KEY: MISC_FEATURE
<222> LOCATION: (3)..(3)
<223> OTHER INFORMATION: X represents any amino acid
<220> FEATURE:
<221> NAME/KEY: MISC_FEATURE
<222> LOCATION: (10)..(10)
<223> OTHER INFORMATION: X represents any amino acid
<220> FEATURE:
<221> NAME/KEY: MISC_FEATURE
<222> LOCATION: (13)..(14)
<223> OTHER INFORMATION: X represents any amino acid
<220> FEATURE:
<221> NAME/KEY: MISC_FEATURE
<222> LOCATION: (17)..(19)
<223> OTHER INFORMATION: X represents any amino acid

<400> SEQUENCE: 11

Thr Gly Xaa Trp Gly Cys Gly Ala Phe Xaa Gly Asp Xaa Xaa Leu Lys
1               5                   10                  15

Xaa Xaa Xaa Gln
            20

<210> SEQ ID NO 12
<211> LENGTH: 13
<212> TYPE: PRT
<213> ORGANISM: Artificial Sequence
<220> FEATURE:
<223> OTHER INFORMATION: Consensus sequence 3 for PARG protein
<220> FEATURE:
<221> NAME/KEY: MISC_FEATURE
<222> LOCATION: (2)..(4)
<223> OTHER INFORMATION: X represents any amino acid
<220> FEATURE:
<221> NAME/KEY: MISC_FEATURE
<222> LOCATION: (6)..(9)
<223> OTHER INFORMATION: X represents any amino acid

<400> SEQUENCE: 12

Asp Xaa Xaa Xaa Arg Xaa Xaa Xaa Xaa Ala Ile Asp Ala
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Consensus sequence 4 for PARG protein
```

-continued

```
<220> FEATURE:
<221> NAME/KEY: MISC_FEATURE
<222> LOCATION: (3)..(4)
<223> OTHER INFORMATION: X represents any amino acid
<220> FEATURE:
<221> NAME/KEY: MISC_FEATURE
<222> LOCATION: (7)..(8)
<223> OTHER INFORMATION: X represents any amino acid

<400> SEQUENCE: 13

Arg Glu Xaa Xaa Lys Ala Xaa Xaa Gly Phe
1               5                   10

<210> SEQ ID NO 14
<211> LENGTH: 11
<212> TYPE: PRT
<213> ORGANISM: Artificial Sequence
<220> FEATURE:
<223> OTHER INFORMATION: conserved PARG region
<220> FEATURE:
<221> NAME/KEY: MISC_FEATURE
<222> LOCATION: (2)..(5)
<223> OTHER INFORMATION: X represents any amino acid
<220> FEATURE:
<221> NAME/KEY: MISC_FEATURE
<222> LOCATION: (7)..(7)
<223> OTHER INFORMATION: X represents any amino acid

<400> SEQUENCE: 14

Gly Xaa Xaa Xaa Xaa Ser Xaa Tyr Thr Gly Tyr
1               5                   10

<210> SEQ ID NO 15
<211> LENGTH: 1530
<212> TYPE: DNA
<213> ORGANISM: Oryza sativa
<220> FEATURE:
<221> NAME/KEY: CDS
<222> LOCATION: (1)..(1530)
<223> OTHER INFORMATION:

<400> SEQUENCE: 15 atg gag gcg cgc ggc gac ctg cgc tcg atc ctg ccc tac ctc ccc gtc      48
Met Glu Ala Arg Gly Asp Leu Arg Ser Ile Leu Pro Tyr Leu Pro Val
1               5                   10                  15 gtg ctc cgc ggc ggc gcg ctc ttc tgg ccg ccg gcg gcg cag gag gcg      96
Val Leu Arg Gly Gly Ala Leu Phe Trp Pro Pro Ala Ala Gln Glu Ala
            20                  25                  30 ctc aag gcg ctg gcg ctg ggc ccc gac gtg agc cgc gtc tcc tcc ggc     144
Leu Lys Ala Leu Ala Leu Gly Pro Asp Val Ser Arg Val Ser Ser Gly
        35                  40                  45 gac gtc ctc gcc gac gcc ctc acc gac ctc cgc ctc gcg ctc aac ctc     192
Asp Val Leu Ala Asp Ala Leu Thr Asp Leu Arg Leu Ala Leu Asn Leu
    50                  55                  60 gac cca ctc ccg cgc cgc gcc gcc gag ggc ttc gcg ctc ttc ttc gac     240
Asp Pro Leu Pro Arg Arg Ala Ala Glu Gly Phe Ala Leu Phe Phe Asp
65                  70                  75                  80 gac ctc ctg tcg cgg gcg cag gcg cgg gac tgg ttc gac cac gtc gcc     288
Asp Leu Leu Ser Arg Ala Gln Ala Arg Asp Trp Phe Asp His Val Ala
                85                  90                  95 ccc tcc ctc gcc cgc ctc ctc ctc cgc ctc ccc acg ctg ctc gag ggc     336
Pro Ser Leu Ala Arg Leu Leu Leu Arg Leu Pro Thr Leu Leu Glu Gly
            100                 105                 110 cac tac cgc gcc gcc ggc gac gag gct cgc ggg ctc cgc atc ctg agc     384
His Tyr Arg Ala Ala Gly Asp Glu Ala Arg Gly Leu Arg Ile Leu Ser
        115                 120                 125
```

|  |  |
|---|---|
| tcg cag gat gcc ggg ctc gtg ctc ctc agc cag gag ctc gcc gcc gcg<br>Ser Gln Asp Ala Gly Leu Val Leu Leu Ser Gln Glu Leu Ala Ala Ala<br>130                       135                     140 | 432 |
| ctg ctc gcc tgc gcg ctc ttc tgc ctg ttc ccc acc gcc gat agg gcc<br>Leu Leu Ala Cys Ala Leu Phe Cys Leu Phe Pro Thr Ala Asp Arg Ala<br>145                       150                     155                     160 | 480 |
| gag gcg tgc ctc ccg gcg atc aat ttc gat agc cta ttt gcg gca ctg<br>Glu Ala Cys Leu Pro Ala Ile Asn Phe Asp Ser Leu Phe Ala Ala Leu<br>                     165                     170                     175 | 528 |
| tgt tat aat tcg agg caa agc cag gag cag aag gtg agg tgc ctt gtt<br>Cys Tyr Asn Ser Arg Gln Ser Gln Glu Gln Lys Val Arg Cys Leu Val<br>                180                     185                     190 | 576 |
| cac tat ttt gac agg gtg acc gct tct aca cct act ggt tcc gtt tcg<br>His Tyr Phe Asp Arg Val Thr Ala Ser Thr Pro Thr Gly Ser Val Ser<br>               195                     200                     205 | 624 |
| ttt gag cgt aag gtt ctt cct cgc cgt cct gaa tct gat ggc att acg<br>Phe Glu Arg Lys Val Leu Pro Arg Arg Pro Glu Ser Asp Gly Ile Thr<br>210                       215                     220 | 672 |
| tac cct gac atg gat act tgg atg aaa tct ggt gtt ccc ctt tgc aca<br>Tyr Pro Asp Met Asp Thr Trp Met Lys Ser Gly Val Pro Leu Cys Thr<br>225                       230                     235                     240 | 720 |
| ttc cgg gta ttt tcc tca ggc ttg ata gaa gat gag gaa caa gaa gcc<br>Phe Arg Val Phe Ser Ser Gly Leu Ile Glu Asp Glu Glu Gln Glu Ala<br>                     245                     250                     255 | 768 |
| ctt gaa gtt gac ttt gca aat aga tat ttg gga ggt ggc gca ctt tcc<br>Leu Glu Val Asp Phe Ala Asn Arg Tyr Leu Gly Gly Gly Ala Leu Ser<br>               260                     265                     270 | 816 |
| aga ggc tgc gtg cag gaa gaa atc cgg ttc atg ata aac cca gaa ttg<br>Arg Gly Cys Val Gln Glu Glu Ile Arg Phe Met Ile Asn Pro Glu Leu<br>                     275                     280                     285 | 864 |
| atc gtg ggc atg ctc ttc atg gtt tca atg gaa gat aat gaa gct ata<br>Ile Val Gly Met Leu Phe Met Val Ser Met Glu Asp Asn Glu Ala Ile<br>290                       295                     300 | 912 |
| gaa att gtt ggt gca gaa agg ttc tca cag tac atg ggg tat ggt tcc<br>Glu Ile Val Gly Ala Glu Arg Phe Ser Gln Tyr Met Gly Tyr Gly Ser<br>305                       310                     315                     320 | 960 |
| tca ttc cgt ttt act ggt gac tac tta gat agc aaa ccc ttt gat gcg<br>Ser Phe Arg Phe Thr Gly Asp Tyr Leu Asp Ser Lys Pro Phe Asp Ala<br>                     325                     330                     335 | 1008 |
| atg ggt aga cgg aaa act agg ata gtg gca att gat gct ttg gac tgt<br>Met Gly Arg Arg Lys Thr Arg Ile Val Ala Ile Asp Ala Leu Asp Cys<br>                     340                     345                     350 | 1056 |
| cca act agg tta cag ttt gaa tct agt ggt ctt cta agg gaa gtg aac<br>Pro Thr Arg Leu Gln Phe Glu Ser Ser Gly Leu Leu Arg Glu Val Asn<br>               355                     360                     365 | 1104 |
| aag gct ttt tgt gga ttt ttg gat caa tca aat cat cag ctc tgt gca<br>Lys Ala Phe Cys Gly Phe Leu Asp Gln Ser Asn His Gln Leu Cys Ala<br>370                       375                     380 | 1152 |
| aag ctt gtc cag gat tta aat aca aag gat aac tgt cca agt gtc att<br>Lys Leu Val Gln Asp Leu Asn Thr Lys Asp Asn Cys Pro Ser Val Ile<br>385                       390                     395                     400 | 1200 |
| cct gat gaa tgc ata gga gtt tca act gga aac tgg ggt tgc ggg gct<br>Pro Asp Glu Cys Ile Gly Val Ser Thr Gly Asn Trp Gly Cys Gly Ala<br>                     405                     410                     415 | 1248 |
| ttt ggt gga aac cct gaa atc aag agc atg att caa tgg att gct gca<br>Phe Gly Gly Asn Pro Glu Ile Lys Ser Met Ile Gln Trp Ile Ala Ala<br>                     420                     425                     430 | 1296 |
| tca cag gca ctc cga tct ttt att aac tac tac act ttt gag tcc gaa<br>Ser Gln Ala Leu Arg Ser Phe Ile Asn Tyr Tyr Thr Phe Glu Ser Glu<br>435                       440                     445 | 1344 |

```
tca ctg aaa aga tta gaa gag gtg acc cag tgg ata ttg cgc cat agg      1392
Ser Leu Lys Arg Leu Glu Glu Val Thr Gln Trp Ile Leu Arg His Arg
    450                 455                 460 tgg acg gtt ggc gag ttg tgg gac atg ctt gtg gag tat tcc tcc cag      1440
Trp Thr Val Gly Glu Leu Trp Asp Met Leu Val Glu Tyr Ser Ser Gln
465                 470                 475                 480 agg cta aga gga gac acc aat gag ggc ttt tta aca tgg cta ctt ccc      1488
Arg Leu Arg Gly Asp Thr Asn Glu Gly Phe Leu Thr Trp Leu Leu Pro
                485                 490                 495 aag gac atc ccc aat ggt gat gta gat tac atg tgt gaa tag              1530
Lys Asp Ile Pro Asn Gly Asp Val Asp Tyr Met Cys Glu
                500                 505

<210> SEQ ID NO 16
<211> LENGTH: 509
<212> TYPE: PRT
<213> ORGANISM: Oryza sativa

<400> SEQUENCE: 16

Met Glu Ala Arg Gly Asp Leu Arg Ser Ile Leu Pro Tyr Leu Pro Val
1               5                   10                  15

Val Leu Arg Gly Gly Ala Leu Phe Trp Pro Ala Ala Gln Glu Ala
            20                  25                  30

Leu Lys Ala Leu Ala Leu Gly Pro Asp Val Ser Arg Val Ser Ser Gly
        35                  40                  45

Asp Val Leu Ala Asp Ala Leu Thr Asp Leu Arg Leu Ala Leu Asn Leu
    50                  55                  60

Asp Pro Leu Pro Arg Arg Ala Ala Glu Gly Phe Ala Leu Phe Phe Asp
65                  70                  75                  80

Asp Leu Leu Ser Arg Ala Gln Ala Arg Asp Trp Phe Asp His Val Ala
                85                  90                  95

Pro Ser Leu Ala Arg Leu Leu Arg Leu Pro Thr Leu Leu Glu Gly
            100                 105                 110

His Tyr Arg Ala Ala Gly Asp Glu Ala Arg Gly Leu Arg Ile Leu Ser
        115                 120                 125

Ser Gln Asp Ala Gly Leu Val Leu Leu Ser Gln Glu Leu Ala Ala Ala
    130                 135                 140

Leu Leu Ala Cys Ala Leu Phe Cys Leu Phe Pro Thr Ala Asp Arg Ala
145                 150                 155                 160

Glu Ala Cys Leu Pro Ala Ile Asn Phe Asp Ser Leu Phe Ala Ala Leu
                165                 170                 175

Cys Tyr Asn Ser Arg Gln Ser Gln Glu Gln Lys Val Arg Cys Leu Val
            180                 185                 190

His Tyr Phe Asp Arg Val Thr Ala Ser Thr Pro Thr Gly Ser Val Ser
        195                 200                 205

Phe Glu Arg Lys Val Leu Pro Arg Arg Pro Glu Ser Asp Gly Ile Thr
    210                 215                 220

Tyr Pro Asp Met Asp Thr Trp Met Lys Ser Gly Val Pro Leu Cys Thr
225                 230                 235                 240

Phe Arg Val Phe Ser Ser Gly Leu Ile Glu Asp Glu Gln Glu Ala
                245                 250                 255

Leu Glu Val Asp Phe Ala Asn Arg Tyr Leu Gly Gly Gly Ala Leu Ser
            260                 265                 270

Arg Gly Cys Val Gln Glu Glu Ile Arg Phe Met Ile Asn Pro Glu Leu
        275                 280                 285
```

```
Ile Val Gly Met Leu Phe Met Val Ser Met Glu Asp Asn Glu Ala Ile
    290                 295                 300

Glu Ile Val Gly Ala Glu Arg Phe Ser Gln Tyr Met Gly Tyr Gly Ser
305                 310                 315                 320

Ser Phe Arg Phe Thr Gly Asp Tyr Leu Asp Ser Lys Pro Phe Asp Ala
                325                 330                 335

Met Gly Arg Arg Lys Thr Arg Ile Val Ala Ile Asp Ala Leu Asp Cys
                340                 345                 350

Pro Thr Arg Leu Gln Phe Glu Ser Ser Gly Leu Leu Arg Glu Val Asn
                355                 360                 365

Lys Ala Phe Cys Gly Phe Leu Asp Gln Ser Asn His Gln Leu Cys Ala
    370                 375                 380

Lys Leu Val Gln Asp Leu Asn Thr Lys Asp Asn Cys Pro Ser Val Ile
385                 390                 395                 400

Pro Asp Glu Cys Ile Gly Val Ser Thr Gly Asn Trp Gly Cys Gly Ala
                405                 410                 415

Phe Gly Gly Asn Pro Glu Ile Lys Ser Met Ile Gln Trp Ile Ala Ala
                420                 425                 430

Ser Gln Ala Leu Arg Ser Phe Ile Asn Tyr Tyr Thr Phe Glu Ser Glu
    435                 440                 445

Ser Leu Lys Arg Leu Glu Glu Val Thr Gln Trp Ile Leu Arg His Arg
450                 455                 460

Trp Thr Val Gly Glu Leu Trp Asp Met Leu Val Glu Tyr Ser Ser Gln
465                 470                 475                 480

Arg Leu Arg Gly Asp Thr Asn Glu Gly Phe Leu Thr Trp Leu Leu Pro
                485                 490                 495

Lys Asp Ile Pro Asn Gly Asp Val Asp Tyr Met Cys Glu
                500                 505

<210> SEQ ID NO 17
<211> LENGTH: 25
<212> TYPE: DNA
<213> ORGANISM: Artificial Sequence
<220> FEATURE:
<223> OTHER INFORMATION: degenerate oligonucleotide primer PG1

<400> SEQUENCE: 17
atgtbccaca rmtckccrac mgtcc                                          25

<210> SEQ ID NO 18
<211> LENGTH: 28
<212> TYPE: DNA
<213> ORGANISM: Artificial Sequence
<220> FEATURE:
<223> OTHER INFORMATION: degenerate oligonucleotide primer PG2

<400> SEQUENCE: 18
gggtytccwc caaaarcmcc rcawcccc                                       28

<210> SEQ ID NO 19
<211> LENGTH: 26
<212> TYPE: DNA
<213> ORGANISM: Artificial Sequence
<220> FEATURE:
<223> OTHER INFORMATION: degenerate oligonucleotide primer PG3

<400> SEQUENCE: 19
gctatagaaa twgtyggtgy rgaaag                                         26
```

```
<210> SEQ ID NO 20
<211> LENGTH: 26
<212> TYPE: DNA
<213> ORGANISM: Artificial Sequence
<220> FEATURE:
<223> OTHER INFORMATION: degenerate oligonucleotide primer PG4

<400> SEQUENCE: 20
agrggstgyg trcaggarga ratmcg                                       26

<210> SEQ ID NO 21
<211> LENGTH: 23
<212> TYPE: DNA
<213> ORGANISM: Artificial Sequence
<220> FEATURE:
<223> OTHER INFORMATION: degenerate oligonucleotide primer PG5
<220> FEATURE:
<221> NAME/KEY: misc_feature
<222> LOCATION: (18)..(18)
<223> OTHER INFORMATION: n=any nucleotide

<400> SEQUENCE: 21
atggargaya aygargcnat hga                                          23

<210> SEQ ID NO 22
<211> LENGTH: 24
<212> TYPE: DNA
<213> ORGANISM: Artificial Sequence
<220> FEATURE:
<223> OTHER INFORMATION: degenerate oligonucleotide primer PG6

<400> SEQUENCE: 22
ccaytgdagc atrctyttda gytc                                         24

<210> SEQ ID NO 23
<211> LENGTH: 603
<212> TYPE: DNA
<213> ORGANISM: zea mays

<400> SEQUENCE: 23
tagggctgtg tgcaggagga aatccgcttc atgataaacc ccgaattgat tgtgggtatg    60
ctattcttgt cttgtatgga agataacgag gctatagaaa tctttggtgc agaacggttc   120
tcacagtata tggttatgg ttcctccttt cgctttgttg gtgactattt agataccaaa    180 cccttttgatt cgatgggcag acggagaact aggattgtgg ctatcgatgc tttggactgt   240
ccagctaggt tacactatga atctggctgt ctcctaaggg aagtgaacaa ggcatttgt     300 ggatttttcg atcaatcgaa acaccatctc tatgcgaagc ttttccagga tttgcacaac   360
aaggatgact tttcaagcat caattccagt gagtacgtag gagtttcaac aggaaactgg   420
ggttgtggtg cttttggtgg aaaccctgaa atcaagagca tgattcagtg gattgctgca   480
tcacaggctc ttcgcccttt tgttaattac tacactttg agaacgtgtc tctgcaaaga    540
ttagaggagg tgatccagtg gatacggctt catggctgga ctgtcggcga gctgtggaac   600
ata                                                                603

<210> SEQ ID NO 24
<211> LENGTH: 12987
<212> TYPE: DNA
<213> ORGANISM: Artificial sequence
<220> FEATURE:
<223> OTHER INFORMATION: T-DNA vector comprising a chimeric ParG
      expression reducing gene
<220> FEATURE:
<221> NAME/KEY: misc_feature
```

```
<222> LOCATION: (1)..(25)
<223> OTHER INFORMATION: complement of Left T-DNA border
<220> FEATURE:
<221> NAME/KEY: misc_feature
<222> LOCATION: (58)..(318)
<223> OTHER INFORMATION: complement of 3' nos
<220> FEATURE:
<221> NAME/KEY: misc_feature
<222> LOCATION: (337)..(888)
<223> OTHER INFORMATION: bar coding region
<220> FEATURE:
<221> NAME/KEY: misc_feature
<222> LOCATION: (889)..(1721)
<223> OTHER INFORMATION: 35S promoter
<220> FEATURE:
<221> NAME/KEY: misc_feature
<222> LOCATION: (1728)..(3123)
<223> OTHER INFORMATION: 35S promoter
<220> FEATURE:
<221> NAME/KEY: misc_feature
<222> LOCATION: (3133)..(3311)
<223> OTHER INFORMATION: part of ParG homologue of Zea mays
<220> FEATURE:
<221> NAME/KEY: misc_feature
<222> LOCATION: (3344)..(4085)
<223> OTHER INFORMATION: Pdk intron
<220> FEATURE:
<221> NAME/KEY: misc_feature
<222> LOCATION: (4119)..(4297)
<223> OTHER INFORMATION: part of ParG homologue of Zea mays (inverted)
<220> FEATURE:
<221> NAME/KEY: misc_feature
<222> LOCATION: (4310)..(5020)
<223> OTHER INFORMATION: 3' OCS
<220> FEATURE:
<221> NAME/KEY: misc_feature
<222> LOCATION: (5066)..(5042)
<223> OTHER INFORMATION: Right T-DNA border

<400> SEQUENCE: 24
cggcaggata tattcaattg taaatggctc catggcgatc gctctagagg atcttcccga      60
tctagtaaca tagatgacac cgcgcgcgat aatttatcct agtttgcgcg ctatattttg     120
ttttctatcg cgtattaaat gtataattgc gggactctaa tcataaaaac ccatctcata     180
aataacgtca tgcattacat gttaattatt acatgcttaa cgtaattcaa cagaaattat     240
atgataatca tcgcaagacc ggcaacagga ttcaatctta agaaacttta ttgccaaatg     300
tttgaacgat ctgcttcgga tcctagacgc gtgagatcag atctcggtga cgggcaggac     360
cggacggggc ggtaccggca ggctgaagtc cagctgccag aaacccacgt catgccagtt     420
cccgtgcttg aagccggccg cccgcagcat gccgcggggg gcatatccga gcgcctcgtg     480
catgcgcacg ctcgggtcgt tgggcagccc gatgacagcg accacgctct tgaagccctg     540
tgcctccagg gacttcagca ggtggtgta gagcgtggag cccagtcccg tccgctggtg     600
gcggggggag acgtacacgg tcgactcggc cgtccagtcg taggcgttgc gtgccttcca     660
ggggcccgcg taggcgatgc cggcgacctc gccgtccacc tcggcgacga gccaggata     720 gcgctcccgc agacggacga ggtcgtccgt ccactcctgc ggttcctgcg gctcggtacg     780
gaagttgacc gtgcttgtct cgatgtagtg gttgacgatg gtgcagaccg ccggcatgtc     840
cgcctcggtg gcacggcgga tgtcggccgg gcgtcgttct gggtccatgg ttatagagag     900
agagatagat ttatagagag agactggtga tttcagcgtg tcctctccaa atgaaatgaa     960
cttccttata tagaggaagg gtcttgcgaa ggatagtggg attgtgcgtc atcccttacg    1020
tcagtggaga tgtcacatca atccacttgc tttgaagacg tggttggaac gtcttctttt    1080
tccacgatgc tcctcgtggg tggggtcca tctttgggac cactgtcggc agaggcatct    1140
```

```
tgaatgatag cctttccttt atcgcaatga tggcatttgt aggagccacc ttccttttct    1200
actgtccttt cgatgaagtg acagatagct gggcaatgga atccgaggag gtttcccgaa    1260
attatccttt gttgaaaagt ctcaatagcc ctttggtctt ctgagactgt atctttgaca    1320
tttttggagt agaccagagt gtcgtgctcc accatgttga cgaagatttt cttcttgtca    1380
ttgagtcgta aaagactctg tatgaactgt tcgccagtct tcacggcgag ttctgttaga    1440
tcctcgattt gaatcttaga ctccatgcat ggccttagat tcagtaggaa ctaccttttt    1500
agagactcca atctctatta cttgccttgg tttatgaagc aagccttgaa tcgtccatac    1560
tggaatagta cttctgatct tgagaaatat gtctttctct gtgttcttga tgcaattagt    1620
cctgaatctt ttgactgcat cttaaccctt cttgggaagg tatttgatct cctggagatt    1680
gttactcggg tagatcgtct tgatgagacc tgctgcgtag gaacgcggcc gcgtatacgt    1740
atcgatatct tcgaattcga gctcgtcgag cggccgctcg acgaattaat tccaatccca    1800
caaaaatctg agcttaacag cacagttgct cctctcagag cagaatcggg tattcaacac    1860
cctcatatca actactacgt tgtgtataac ggtccacatg ccggtatata cgatgactgg    1920
ggttgtacaa aggcggcaac aaacggcgtt cccggagttg cacacaagaa atttgccact    1980
attacagagg caagagcagc agctgacgcg tacacaacaa gtcagcaaac agacaggttg    2040
aacttcatcc ccaaaggaga agctcaactc aagcccaaga gctttgctaa ggccctaaca    2100
agcccaccaa agcaaaaagc ccactggctc acgctaggaa ccaaaaggcc cagcagtgat    2160
ccagccccaa aagagatctc ctttgccccg gagattacaa tggacgattt cctctatctt    2220
tacgatctag gaaggaagtt cgaaggtgaa ggtgacgaca ctatgttcac cactgataat    2280
gagaaggtta gcctcttcaa tttcagaaag aatgctgacc cacagatggt tagagaggcc    2340
tacgcagcag gtctcatcaa gacgatctac ccgagtaaca atctccagga gatcaaatac    2400
cttcccaaga aggttaaaga tgcagtcaaa agattcagga ctaattgcat caagaacaca    2460
gagaaagaca tatttctcaa gatcagaagt actattccag tatggacgat tcaaggcttg    2520
cttcataaac caaggcaagt aatagagatt ggagtctcta aaaaggtagt tcctactgaa    2580
tctaaggcca tgcatggagt ctaagattca atcgaggat ctaacagaac tcgccgtgaa    2640
gactggcgaa cagttcatac agagtctttt acgactcaat gacaagaaga aaatcttcgt    2700
caacatggtg gagcacgaca ctctggtcta ctccaaaaat gtcaaagata cagtctcaga    2760
agaccaaagg gctattgaga cttttcaaca aaggataatt tcgggaaacc tcctcggatt    2820
ccattgccca gctatctgtc acttcatcga aggacagta gaaaaggaag gtggctccta    2880
caaatgccat cattgcgata aaggaaaggc tatcattcaa gatctctctg ccgacagtgg    2940
tcccaaagat ggacccccac ccacgaggag catcgtggaa aagaagacg ttccaaccac    3000 gtcttcaaag caagtggatt gatgtgacat ctccactgac gtaagggatg acgcacaatc    3060
ccactatcct tcgcaagacc cttcctctat ataaggaagt tcatttcatt tggagaggac    3120
acgctcgagc ccgaattgat tgtgggtatg ctattcttgt cttgtatgga agataacgag    3180
gctatagaaa tctttggtgc agaacggttc tcacagtata tgggttatgg ttcctccttt    3240
cgctttgttg gtgactattt agataccaaa cccttgatt cgatgggcag acggagaact    3300
aggattgtgg cggtaccca gcttggtaag gaaataatta ttttcttttt tccttttagt    3360
ataaaatagt taagtgatgt taattagtat gattataata atatagttgt tataattgtg    3420
aaaaaataat ttataaatat attgtttaca taaacaacat agtaatgtaa aaaaatatga    3480
caagtgatgt gtaagacgaa gaagataaaa gttgagagta agtatattat ttttaatgaa    3540
```

```
tttgatcgaa catgtaagat gatatactag cattaatatt tgttttaatc ataatagtaa    3600
ttctagctgg tttgatgaat taaatatcaa tgataaaata ctatagtaaa aataagaata    3660
aataaattaa aataatattt ttttatgatt aatagtttat tatataatta aatatctata    3720
ccattactaa atattttagt ttaaaagtta ataaatattt tgttagaaat tccaatctgc    3780
ttgtaattta tcaataaaca aaatattaaa taacaagcta agtaacaaa taatatcaaa     3840 ctaatagaaa cagtaatcta atgtaacaaa acataatcta atgctaatat aacaaagcgc    3900
aagatctatc attttatata gtattatttt caatcaacat tcttattaat ttctaaataa    3960
tacttgtagt tttattaact tctaaatgga ttgactatta attaaatgaa ttagtcgaac    4020
atgaataaac aaggtaacat gatagatcat gtcattgtgt tatcattgat cttacatttg    4080
gattgattac agttgggaag ctgggttcga aatcgatagc cacaatccta gttctccgtc    4140
tgcccatcga atcaagggt ttggtatcta aatagtcacc aacaaagcga aggaggaac     4200 cataacccat atactgtgag aaccgttctg caccaaagat ttctatagcc tcgttatctt    4260
ccatacaaga caagaatagc atacccacaa tcaattcggg tctagagtcc tgctttaatg    4320
agatatgcga gacgcctatg atcgcatgat atttgctttc aattctgttg tgcacgttgt    4380
aaaaaacctg agcatgtgta gctcagatcc ttaccgccgg tttcggttca ttctaatgaa    4440
tatatcaccc gttactatcg tatttttatg aataatattc tccgttcaat ttactgattg    4500
taccctacta cttatatgta caatattaaa atgaaaacaa tatattgtgc tgaataggtt    4560 tatacgaca tctatgatag agcgccacaa taacaaacaa ttgcgtttta ttattacaaa     4620 tccaattta aaaaaagcgg cagaaccggt caaacctaaa agactgatta cataaatctt     4680
attcaaattt caaaaggccc caggggctag tatctacgac acaccgagcg gcgaactaat    4740
aacgttcact gaagggaact ccggttcccc gccggcgcgc atgggtgaga ttccttgaag    4800
ttgagtattg gccgtccgct ctaccgaaag ttacgggcac cattcaaccc ggtccagcac    4860
ggcggccggg taaccgactt gctgccccga gaattatgca gcattttttt ggtgtatgtg    4920
ggccccaaat gaagtgcagg tcaaaccttg acagtgacga caaatcgttg gcgggtcca    4980 gggcgaattt tgcgacaaca tgtcgaggct cagcaggacc tgcaggtcga cggccgagta    5040
ctggcaggat atataccgtt gtaatttgtc gcgtgtgaat aagtcgctgt gtatgtttgt    5100
ttgattgttt ctgttggagt gcagcccatt tcaccggaca agtcggctag attgatttag    5160
ccctgatgaa ctgccgaggg gaagccatct tgagcgcgga atgggaatgg atttcgttgt    5220
acaacgagac gacagaacac ccacgggacc gagcttcgat cgagcatcaa atgaaactgc    5280
aatttattca tatcaggatt atcaatacca tattttgaa aaagccgttt ctgtaatgaa     5340
ggagaaaact caccgaggca gttccatagg atggcaagat cctggtatcg gtctgcgatt    5400
ccgactcgtc caacatcaat acaacctatt aatttcccct cgtcaaaaat aaggttatca    5460
agtgagaaat caccatgagt gacgactgaa tccggtgaga atggcaaaag tttatgcatt    5520
tctttccaga cttgttcaac aggccagcca ttacgctcgt catcaaaatc actcgcatca    5580
accaaaccgt tattcattcg tgattgcgcc tgagcgagac gaaatacgcc gctgttaaaa    5640
ggacaattac aaacaggaat cgaatgcaac cggcgcagga acactgccag cgcatcaaca    5700
atattttcac ctgaatcagg atattcttct aatacctgga atgctgtttt tccggggatc    5760
gcagtggtga gtaaccatgc atcatcagga gtacggataa aatgcttgat ggtcggaaga    5820
ggcataaatt ccgtcagcca gtttagtctg accatctcat ctgtaacatc attggcaacg    5880
```

```
ctacctttgc catgtttcag aaacaactct ggcgcatcgg gcttcccata caatcgatag    5940
attgtcgcac ctgattgccc gacattatcc gaatctggca attccggttc gcttgctgtc    6000
cataaaaccg cccagtctag ctatcgccat gtaagcccac tgcaagctac ctgctttctc    6060
tttgcgcttg cgttttccgg atcttcttga gatccttttt ttctgcgcgt aatctgctgc    6120
ttgcaaacaa aaaaaccacc gctaccagcg gtggtttgtt tgccggatca agagctacca    6180
actcttttc cgaaggtaac tggcttcagc agagcgcaga taccaaatac tgtccttcta    6240
gtgtagccgt agttaggcca ccacttcaag aactctgtag caccgcctac atacctcgct    6300
ctgctaatcc tgttaccagt ggctgctgcc agtggcgata gtcgtgtct taccgggttg     6360
gactcaagac gatagttacc ggataaggcg cagcggtcgg gctgaacggg gggttcgtgc    6420
acacagccca gcttggagcg aacgacctac accgaactga gatacctaca gcgtgagcta    6480
tgagaaagcg ccacgcttcc cgaagggaga aaggcggaca ggtatccggt aagcggcagg    6540
gtcggaacag gagagcgcac gagggagctt ccagggggaa acgcctggta tctttatagt    6600
cctgtcgggt ttcgccacct ctgacttgag cgtcgatttt tgtgatgctc gtcagggggg    6660
cggagcctat ggaaaaacgc cagcaacgcg gccttttac ggttcctggc cttttgctgg     6720
ccttttgctc acatgttctt tcctgcgtta tcccctgatt ctgtggataa ccgtattacc    6780
gcctttgagt gagctgatac cgctcgccgc agccgaacga ccgagcgcag cgagtcagtg    6840
agcgaggaag cggaagagcg cctgatgcgg tattttctcc ttacgcatct gtgcggtatt    6900
tcacaccgca tatggtgcac tctcagtaca atctgctctg atgccgcata gttaagccag    6960
tatacactcc gctatcgcta cgtgactggg tcatggctgc gccccgacac ccgccaacac    7020
ccgctgacgc gccctgacgg gcttgtctgc tcccggcatc cgcttacaga caagctgtga    7080
ccgtctccgg gagctgcatg tgtcagaggt tttcaccgtc atcaccgaaa cgcgcgaggc    7140
agggtgcctt gatgtgggcg ccggcggtcg agtggcgacg cgcgcggcttg tccgcgccct    7200
ggtagattgc ctggccgtag gccagccatt tttgagcggc cagcggccgc gataggccga    7260
cgcgaagcgg cggggcgtag ggagcgcagc gaccgaaggg taggcgcttt ttgcagctct    7320
tcggctgtgc gctggccaga cagttatgca caggccaggc gggttttaag agttttaata    7380
agttttaaag agtttaggc ggaaaaatcg ccttttttct cttttatatc agtcacttac      7440
atgtgtgacc ggttcccaat gtacggcttt gggttcccaa tgtacgggtt ccggttccca    7500
atgtacggct ttgggttccc aatgtacgtg ctatccacag gaaagagacc ttttcgacct    7560
tttttcccctg ctagggcaat tgccctagc atctgctccg tacattagga accggcggat    7620
gcttcgccct cgatcaggtt gcggtagcgc atgactagga tcgggccagc ctgccccgcc    7680
tcctccttca aatcgtactc cggcaggtca tttgacccga tcagcttgcg cacggtgaaa    7740
cagaacttct tgaactctcc ggcgctgcca ctgcgttcgt agatcgtctt gaacaaccat    7800
ctggcttctg ccttgcctgc ggcgcggcgt gccaggcggt agagaaaacg gccgatgccg    7860
ggatcgatca aaaagtaatc ggggtgaacc gtcagcacgt ccgggttctt gccttctgtg    7920
atctcgcggt acatccaatc agctagctcg atctcgatgt actccggccg cccggtttcg    7980
ctctttacga tcttgtagcg gctaatcaag gcttcaccct cggataccgt caccaggcgg    8040
ccgttcttgg ccttcttcgt acgctgcatg caacgtgctg tggtgtttaa ccgaatgcag    8100
gtttctacca ggtcgtcttt ctgctttccg ccatcggctc gccggcagaa cttgagtacg    8160
tccgcaacgt gtggacggaa cacgcggccg ggcttgtctc ccttcccttc ccggtatcgg    8220
ttcatggatt cggttagatg ggaaaccgcc atcagtacca ggtcgtaatc ccacacactg    8280
```

```
gccatgccgg ccggccctgc ggaaacctct acgtgcccgt ctggaagctc gtagcggatc   8340
acctcgccag ctcgtcggtc acgcttcgac agacggaaaa cggccacgtc catgatgctg   8400
cgactatcgc gggtgcccac gtcatagagc atcggaacga aaaaatctgg ttgctcgtcg   8460
cccttgggcg gcttcctaat cgacggcgca ccggctgccg gcggttgccg ggattctttg   8520
cggattcgat cagcggccgc ttgccacgat tcaccgggc gtgcttctgc ctcgatgcgt   8580
tgccgctggg cggcctgcgc ggccttcaac ttctccacca ggtcatcacc cagcgccgcg   8640
ccgatttgta ccgggccgga tggtttgcga ccgtcacgcc gattcctcgg gcttgggggt   8700
tccagtgcca ttgcagggcc ggcagacaac ccagccgctt acgcctggcc aaccgcccgt   8760
tcctccacac atggggcatt ccacggcgtc ggtgcctggt tgttcttgat tttccatgcc   8820
gcctccttta gccgctaaaa ttcatctact catttattca tttgctcatt tactctggta   8880
gctgcgcgat gtattcagat agcagctcgg taatggtctt gccttggcgt accgcgtaca   8940
tcttcagctt ggtgtgatcc tccgccggca actgaaagtt gacccgcttc atggctggcg   9000
tgtctgccag gctggccaac gttgcagcct tgctgctgcg tgcgctcgga cggccggcac   9060
ttagcgtgtt tgtgcttttg ctcatttcct ctttacctca ttaactcaaa tgagttttga   9120
tttaatttca gcggccagcg cctggacctc gcgggcagcg tcgccctcgg gttctgattc   9180
aagaacggtt gtgccggcgg cggcagtgcc tgggtagctc acgcgctgcg tgatacggga   9240
ctcaagaatg ggcagctcgt acccggccag cgcctcggca acctcaccgc cgatgcgcgt   9300
gcctttgatc gcccgcgaca cgacaaaggc cgcttgtagc cttccatccg tgacctcaat   9360
gcgctgctta accagctcca ccaggtcggc ggtggcccat atgtcgtaag ggcttggctg   9420
caccggaatc agcacgaagt cggctgcctt gatcgcggac acagccaagt ccgccgcctg   9480
gggcgctccg tcgatcacta cgaagtcgcg ccggccgatg gccttcacgt cgcggtcaat   9540 cgtcgggcg tcgatgccga caacggttag cggttgatct tcccgcacgg ccgcccaatc   9600
gcgggcactg ccctggggat cggaatcgac taacagaaca tcggccccgg cgagttgcag   9660
ggcgcgggct agatgggttg cgatggtcgt cttgcctgac ccgcctttct ggttaagtac   9720
agcgataacc ttcatgcgtt cccctttgcgt atttgtttat ttactcatcg catcatatac   9780
gcagcgaccg catgacgcaa gctgttttac tcaaatacac atcaccttt tagacgcgg    9840 cgctcggttt cttcagcggc caagctggcc ggccaggccg ccagcttggc atcagacaaa   9900
ccggccagga tttcatgcag ccgcacggtt gagacgtgcg cggcggctc gaacacgtac    9960 ccggccgcga tcatctccgc ctcgatctct tcggtaatga aaaacggttc gtcctggccg   10020
tcctggtgcg gtttcatgct tgttcctctt ggcgttcatt tcggcggcc gccagggcgt   10080 cggcctcggt caatgcgtcc tcacggaagg caccgcgccg cctggcctcg gtgggcgtca   10140
cttcctcgct gcgctcaagt gcgcggtaca gggtcgagcg atgcacgcca agcagtcag    10200 ccgcctcttt cacggtgcgg ccttcctggt cgatcagctc gcgggcgtgc gcgatctgtg   10260
ccggggtgag ggtagggcgg gggccaaact tcacgcctcg ggccttggcg gcctcgcgcc   10320
cgctccgggt gcggtcgatg attagggaac gctcgaactc ggcaatgccg gcgaacacgg   10380
tcaacaccat gcggccggcc ggcgtggtgg tgtcggccca cggctctgcc aggctacgca   10440
ggcccgcgcc ggcctcctgg atgcgctcgg caatgtccag taggtcgcgg gtgctgcggg   10500
ccaggcggtc tagcctggtc actgtcacaa cgtcgccagg gcgtaggtgg tcaagcatcc   10560
tggccagctc cgggcggtcg cgcctggtgc cggtgatctt ctcggaaaac agcttggtgc   10620
```

```
agccggccgc gtgcagttcg gcccgttggt tggtcaagtc ctggtcgtcg gtgctgacgc  10680
gggcatagcc cagcaggcca gcggcggcgc tcttgttcat ggcgtaatgt ctccggttct  10740
agtcgcaagt attctacttt atgcgactaa aacacgcgac aagaaaacgc caggaaaagg  10800
gcagggcggc agcctgtcgc gtaacttagg acttgtgcga catgtcgttt tcagaagacg  10860
gctgcactga acgtcagaag ccgactgcac tatagcagcg aggggttgg atcgatccct  10920
gctcgcgcag gctgggtgcc aagctctcgg gtaacatcaa ggcccgatcc ttggagccct  10980
tgccctcccg cacgatgatc gtgccgtgat cgaaatccag atccttgacc cgcagttgca  11040
aaccctcact gatccgcatg cccgttccat acagaagctg ggcgaacaaa cgatgctcgc  11100
cttccagaaa accgaggatg cgaaccactt catccggggt cagcaccacc ggcaagcgcc  11160
cggacggcc aggtcttccg atctcctgaa gccaggggca atccgtgcac agcacttgcc  11220
gtagaagaac agcaaggccg ccaatgcctg acgatgcgtg gagaccgaaa ccttgcgctc  11280
gttcgccagc caggacagaa atgcctcgac ttcgctgctg cccaaggttg ccgggtgacg  11340
cacaccgtgg aaacggatga aggcacgaac ccagtggaca taagcctgtt cggttcgtaa  11400
gctgtaatgc aagtagcgta tgcgctcacg caactggtcc agaacttga ccgaacgcag  11460
cggtggtaac ggcgcagtgg cggttttcat ggcttgttat gactgttttt ttggggtaca  11520
gtctatgcct cgggcatcca agcagcaagc gcgttacgcc gtgggtcgat gtttgatgtt  11580
atggagcagc aacgatgtta cgcagcaggg cagtcgccct aaaacaaagt taaacatcat  11640
gagggaagcg gtgatcgccg aagtatcgac tcaactatca gaggtagttg gcgtcatcga  11700
gcgccatctc gaaccgacgt tgctggccgt acatttgtac ggctccgcag tggatggcgg  11760
cctgaagcca cacagtgata ttgatttgct ggttacggtg accgtaaggc ttgatgaaac  11820
aacgcggcga gctttgatca acgacctttt ggaaacttcg gcttccctg gagagagcga  11880
gattctccgc gctgtagaag tcaccattgt tgtgcacgac gacatcattc cgtggcgtta  11940
tccagctaag cgcgaactgc aatttggaga atggcagcgc aatgacattc ttgcaggtat  12000
cttcgagcca gccacgatcg acattgatct ggctatcttg ctgacaaaag caagagaaca  12060
tagcgttgcc ttggtaggtc cagcggcgga ggaactcttt gatccggttc ctgaacagga  12120
tctatttgag gcgctaaatg aaaccttaac gctatggaac tcgccgcccg actgggctgg  12180
cgatgagcga aatgtagtgc ttacgttgtc ccgcatttgg tacagcgcag taaccggcaa  12240
aatcgcgccg aaggatgtcg ctgccgactg gcaatggag cgcctgccgg cccagtatca  12300
gcccgtcata cttgaagcta gacaggctta tcttggacaa gaagaagatc gcttggcctc  12360
gcgcgcagat cagttggaag aatttgtcca ctacgtgaaa ggcgagatca ccaaggtagt  12420
cggcaaataa tgtctaacaa ttcgttcaag ccgacgccg ttcgcggcgc ggcttaactc  12480
aagcgttaga tgcactaagc acataattgc tcacagccaa actatcaggt caagtctgct  12540
tttattattt ttaagcgtgc ataataagcc ctacacaaat tgggagatat atcatgaaag  12600
gctggctttt tcttgttatc gcaatagttg gcgaagtaat cgcaacatcc gcattaaaat  12660
ctagcgaggg ctttactaag ctagcttgct tggtcgttcc ggtaccgtga acgtcggctc  12720
gattgtacct gcgttcaaat actttgcgat cgtgttgcgc gcctgccgg tgcgtcggct  12780
gatctcacg atcgactgct tctctcgcaa cgccatccga cggatgatgt ttaaaagtcc  12840
catgtggatc actccgttgc cccgtcgctc accgtgttgg ggggaaggtg cacatggctc  12900
agttctcaat ggaaattatc tgcctaaccg gctcagttct gcgtagaaac caacatgcaa  12960
gctccaccgg gtgcaaagcg gcagcgg                                      12987
```

<210> SEQ ID NO 25
<211> LENGTH: 13226
<212> TYPE: DNA
<213> ORGANISM: Artificial sequence
<220> FEATURE:
<223> OTHER INFORMATION: T-DNA vector comprising a chimeric ParG
    expression reducing gene
<220> FEATURE:
<221> NAME/KEY: misc_feature
<222> LOCATION: (1)..(25)
<223> OTHER INFORMATION: Left T-DNA border (C)
<220> FEATURE:
<221> NAME/KEY: misc_feature
<222> LOCATION: (58)..(318)
<223> OTHER INFORMATION: 3' nos (C)
<220> FEATURE:
<221> NAME/KEY: misc_feature
<222> LOCATION: (337)..(888)
<223> OTHER INFORMATION: bar coding region (C)
<220> FEATURE:
<221> NAME/KEY: misc_feature
<222> LOCATION: (889)..(1721)
<223> OTHER INFORMATION: 35S3 promoter region (C)
<220> FEATURE:
<221> NAME/KEY: misc_feature
<222> LOCATION: (1778)..(3123)
<223> OTHER INFORMATION: 35S promoter region
<220> FEATURE:
<221> NAME/KEY: misc_feature
<222> LOCATION: (3130)..(3431)
<223> OTHER INFORMATION: part of ParG homologue of Zea mays
<220> FEATURE:
<221> NAME/KEY: misc_feature
<222> LOCATION: (3464)..(4205)
<223> OTHER INFORMATION: Pdk-intron
<220> FEATURE:
<221> NAME/KEY: misc_feature
<222> LOCATION: (4238)..(4536)
<223> OTHER INFORMATION: part of ParG homologue of Zea mays (C)
<220> FEATURE:
<221> NAME/KEY: misc_feature
<222> LOCATION: (4549)..(5259)
<223> OTHER INFORMATION: 3' ocs
<220> FEATURE:
<221> NAME/KEY: misc_feature
<222> LOCATION: (5281)..(5305)
<223> OTHER INFORMATION: Right T-dNA border (C)

<400> SEQUENCE: 25
cggcaggata tattcaattg taaatggctc catggcgatc gctctagagg atcttcccga     60
tctagtaaca tagatgacac cgcgcgcgat aatttatcct agtttgcgcg ctatattttg    120
ttttctatcg cgtattaaat gtataattgc gggactctaa tcataaaaac ccatctcata    180
aataacgtca tgcattacat gttaattatt acatgcttaa cgtaattcaa cagaaattat    240
atgataatca tcgcaagacc ggcaacagga ttcaatctta agaaacttta ttgccaaatg    300
tttgaacgat ctgcttcgga tcctagacgc gtgagatcag atctcggtga cgggcaggac    360
cggacggggc ggtaccggca ggctgaagtc cagctgccag aaacccacgt catgccagtt    420
cccgtgcttg aagccggccg cccgcagcat gccgcggggg gcatatccga gcgcctcgtg    480
catgcgcacg ctcgggtcgt tgggcagccc gatgacagcg accacgctct tgaagccctg    540
tgcctccagg gacttcagca ggtgggtgta gagcgtggag cccagtcccg tccgctggtg    600
gcggggggag acgtacacgg tcgactcggc cgtccagtcg taggcgttgc gtgccttcca    660
ggggcccgcg taggcgatgc cggcgacctc gccgtccacc tcggcgacga gccagggata    720
gcgctcccgc agacgacgga ggtcgtccgt ccactcctgc ggttcctgcg gctcggtacg    780
gaagttgacc gtgcttgtct cgatgtagtg gttgacgatg gtgcagaccg ccggcatgtc    840

```
cgcctcggtg gcacggcgga tgtcggccgg gcgtcgttct gggtccatgg ttatagagag    900
agagatagat ttatagagag agactggtga tttcagcgtg tcctctccaa atgaaatgaa    960
cttccttata tagaggaagg gtcttgcgaa ggatagtggg attgtgcgtc atcccttacg   1020
tcagtggaga tgtcacatca atccacttgc tttgaagacg tggttggaac gtcttctttt   1080
tccacgatgc tcctcgtggg tggggtcca tctttgggac cactgtcggc agaggcatct    1140
tgaatgatag cctttccttt atcgcaatga tggcatttgt aggagccacc ttccttttct   1200
actgtccttt cgatgaagtg acagatagct gggcaatgga atccgaggag gtttcccgaa   1260
attatccttt gttgaaaagt ctcaatagcc ctttggtctt ctgagactgt atctttgaca   1320
tttttggagt agaccagagt gtcgtgctcc accatgttga cgaagatttt cttcttgtca   1380
ttgagtcgta aaagactctg tatgaactgt tcgccagtct tcacggcgag ttctgttaga   1440
tcctcgattt gaatcttaga ctccatgcat ggccttagat tcagtaggaa ctacctttt    1500
agagactcca atctctatta cttgccttgg tttatgaagc aagccttgaa tcgtccatac   1560
tggaatagta cttctgatct tgagaaatat gtctttctct gtgttcttga tgcaattagt   1620
cctgaatctt ttgactgcat cttaaccctt cttgggaagg tatttgatct cctggagatt   1680
gttactcggg tagatcgtct tgatgagacc tgctgcgtag gaacgcggcc gcgtatacgt   1740
atcgatatct tcgaattcga gctcgtcgag cggccgctcg acgaattaat tccaatccca   1800
caaaaatctg agcttaacag cacagttgct cctctcagag cagaatcggg tattcaacac   1860
cctcatatca actactacgt tgtgtataac ggtccacatg ccggtatata cgatgactgg   1920
ggttgtacaa aggcggcaac aaacggcgtt cccggagttg cacacaagaa atttgccact   1980
attacagagg caagagcagc agctgacgcg tacacaacaa gtcagcaaac agacaggttg   2040
aacttcatcc ccaaaggaga agctcaactc aagcccaaga gctttgctaa ggccctaaca   2100
agcccaccaa agcaaaaagc ccactggctc acgctaggaa ccaaaaggcc cagcagtgat   2160
ccagccccaa aagagatctc ctttgccccg gagattacaa tggacgattt cctctatctt   2220
tacgatctag gaaggaagtt cgaaggtgaa ggtgacgaca ctatgttcac cactgataat   2280
gagaaggtta gcctcttcaa tttcagaaag aatgctgacc cacagatggt tagagaggcc   2340
tacgcagcag gtctcatcaa gacgatctac ccgagtaaca atctccagga gatcaaatac   2400
cttcccaaga aggttaaaga tgcagtcaaa agattcagga ctaattgcat caagaacaca   2460
gagaaagaca tatttctcaa gatcagaagt actattccag tatggacgat tcaaggcttg   2520
cttcataaac caaggcaagt aatagagatt ggagtctcta aaaaggtagt tcctactgaa   2580
tctaaggcca tgcatggagt ctaagattca aatcgaggat ctaacagaac tcgccgtgaa   2640
gactggcgaa cagttcatac agagtctttt acgactcaat gacaagaaga aaatcttcgt   2700
caacatggtg gagcacgaca ctctggtcta ctccaaaaat gtcaaagata cagtctcaga   2760
agaccaaagg gctattgaga cttttcaaca aaggataatt tcgggaaacc tcctcggatt   2820
ccattgccca gctatctgtc acttcatcga aaggacagta gaaaggaag gtggctccta   2880
caaatgccat cattgcgata aaggaaaggc tatcattcaa gatctctctg ccgacagtgg   2940
tcccaaagat ggaccccac ccacgaggag catcgtggaa aaagaagacg ttccaaccac   3000
gtcttcaaag caagtggatt gatgtgacat ctccactgac gtaagggatg acgcacaatc   3060
ccactatcct tcgcaagacc cttcctctat ataaggaagt tcatttcatt tggagaggac   3120
acgctcgagg aatctggctg tctcctaagg gaagtgaaca aggcattttg tggattttc   3180
```

```
gatcaatcga aacaccatct ctatgcgaag cttttccagg atttgcacaa caaggatgac    3240
ttttcaagca tcaattccag tgagtacgta ggagtttcaa caggaaactg gggttgtggt    3300
gcttttggtg gaaaccctga aatcaagagc atgattcagt ggattgctgc atcacaggct    3360
cttcgccctt ttgttaatta ctacactttt gagaacgtgt ctctgcaaag attagaggag    3420
gtgatccagt gggtacccca gcttggtaag gaaataatta ttttcttttt tccttttagt    3480
ataaaatagt taagtgatgt taattagtat gattataata atatagttgt tataattgtg    3540
aaaaaataat ttataaatat attgtttaca taaacaacat agtaatgtaa aaaaatatga    3600
caagtgatgt gtaagacgaa gaagataaaa gttgagagta agtatattat ttttaatgaa    3660
tttgatcgaa catgtaagat gatatactag cattaatatt tgttttaatc ataatagtaa    3720
ttctagctgg tttgatgaat taaatatcaa tgataaaata ctatagtaaa aataagaata    3780
aataaattaa aataatattt ttttatgatt aatagtttat tatataatta aatatctata    3840
ccattactaa atattttagt ttaaaagtta ataaatattt tgttagaaat tccaatctgc    3900
ttgtaattta tcaataaaca aaatattaaa taacaagcta agtaacaaa taatatcaaa    3960 ctaatagaaa cagtaatcta atgtaacaaa acataatcta atgctaatat aacaaagcgc    4020
aagatctatc attttatata gtattatttt caatcaacat tcttattaat ttctaaataa    4080
tacttgtagt tttattaact tctaaatgga ttgactatta attaaatgaa ttagtcgaac    4140
atgaataaac aaggtaacat gatagatcat gtcattgtgt tatcattgat cttacatttg    4200
gattgattac agttgggaag ctgggttcga aatcgatcac tggatcacct cctctaatct    4260
ttgcagagac acgttctcaa aagtgtagta attaacaaaa gggcgaagag cctgtgatgc    4320
agcaatccac tgaatcatgc tcttgatttc agggtttcca ccaaaagcac cacaaccccca    4380 gtttcctgtt gaaactccta cgtactcact ggaattgatg cttgaaaagt catccttgtt    4440
gtgcaaatcc tggaaaagct tcgcatagag atggtgtttc gattgatcga aaaatccaca    4500
aaatgccttg ttcacttccc ttaggagaca gccagattct ctagagtcct gctttaatga    4560
gatatgcgag acgcctatga tcgcatgata tttgctttca attctgttgt gcacgttgta    4620
aaaaacctga gcatgtgtag ctcagatcct taccgccggt ttcggttcat tctaatgaat    4680
atatcacccg ttactatcgt atttttatga ataatattct ccgttcaatt tactgattgt    4740
accctactac ttatatgtac aatattaaaa tgaaacaat atattgtgct gaataggttt    4800
atagcgacat ctatgataga gcgccacaat aacaaacaat tgcgttttat tattacaaat    4860 ccaatttttaa aaaagcggc agaaccggtc aaacctaaaa gactgattac ataaatctta    4920
ttcaaatttc aaaaggcccc aggggctagt atctacgaca caccgagcgg cgaactaata    4980
acgttcactg aagggaactc cggttccccg ccggcgcgca tgggtgagat tccttgaagt    5040
tgagtattgg ccgtccgctc taccgaaagt tacgggcacc attcaacccg gtccagcacg    5100
gcggccgggt aaccgacttg ctgccccgag aattatgcag cattttttg tgtatgtgg    5160 gccccaaatg aagtgcaggt caaaccttga cagtgacgac aaatcgttgg gcgggtccag    5220
ggcgaatttt gcgacaacat gtcgaggctc agcaggacct gcaggtcgac ggccgagtac    5280
tggcaggata tataccgttg taatttgtcg cgtgtgaata agtcgctgtg tatgtttgtt    5340
tgattgtttc tgttggagtg cagcccattt caccggacaa gtcggctaga ttgatttagc    5400
cctgatgaac tgccgagggg aagccatctt gagcgcggaa tgggaatgga tttcgttgta    5460
caacgagacg acagaacacc cacgggaccg agcttcgatc gagcatcaaa tgaaactgca    5520
atttattcat atcaggatta tcaataccat attttttgaaa aagccgtttc tgtaatgaag    5580
```

```
gagaaaactc accgaggcag ttccatagga tggcaagatc ctggtatcgg tctgcgattc    5640
cgactcgtcc aacatcaata caacctatta atttcccctc gtcaaaaata aggttatcaa    5700
gtgagaaatc accatgagtg acgactgaat ccggtgagaa tggcaaaagt ttatgcattt    5760
ctttccagac ttgttcaaca ggccagccat tacgctcgtc atcaaaatca ctcgcatcaa    5820
ccaaaccgtt attcattcgt gattgcgcct gagcgagacg aaatacgccg ctgttaaaag    5880
gacaattaca aacaggaatc gaatgcaacc ggcgcaggaa cactgccagc gcatcaacaa    5940
tattttcacc tgaatcagga tattcttcta atacctggaa tgctgttttt ccggggatcg    6000
cagtggtgag taaccatgca tcatcaggag tacggataaa atgcttgatg gtcggaagag    6060
gcataaattc cgtcagccag tttagtctga ccatctcatc tgtaacatca ttggcaacgc    6120
tacctttgcc atgtttcaga acaactctg gcgcatcggg cttcccatac aatcgataga    6180
ttgtcgcacc tgattgcccg acattatccg aatctggcaa ttccggttcg cttgctgtcc    6240
ataaaaccgc ccagtctagc tatcgccatg taagcccact gcaagctacc tgctttctct    6300
ttgcgcttgc gttttccgga tcttcttgag atcctttttt tctgcgcgta atctgctgct    6360
tgcaaacaaa aaaccaccg ctaccagcgg tggtttgttt gccggatcaa gagctaccaa    6420 ctcttttttcc gaaggtaact ggcttcagca gagcgcagat accaaatact gtccttctag    6480
tgtagccgta gttaggccac cacttcaaga actctgtagc accgcctaca tacctcgctc    6540
tgctaatcct gttaccagtg gctgctgcca gtggcgataa gtcgtgtctt accgggttgg    6600
actcaagacg atagttaccg gataaggcgc agcggtcggg ctgaacgggg ggttcgtgca    6660
cacagcccag cttggagcga acgacctaca ccgaactgag atacctacag cgtgagctat    6720
gagaaagcgc cacgcttccc gaaggagaa aggcggacag tatccggta gcggcaggg    6780 tcggaacagg agagcgcacg agggagcttc caggggaaa cgcctggtat ctttatagtc    6840
ctgtcgggtt tcgccacctc tgacttgagc gtcgatttt tgtgatgctcg tcagggggc    6900 ggagcctatg gaaaaacgcc agcaacgcgg ccttttttacg gttcctggcc tttgctggc    6960 cttttgctca catgttctttt cctgcgttat cccctgattc tgtggataac cgtattaccg    7020
cctttgagtg agctgatacc gctcgccgca gccgaacgac cgagcgcagc gagtcagtga    7080
gcgaggaagc ggaagagcgc ctgatgcggt attttctcct tacgcatctg tgcggtatt     7140 cacaccgcat atggtgcact ctcagtacaa tctgctctga tgccgcatag ttaagccagt    7200
atacactccg ctatcgctac gtgactgggt catggctgcg ccccgacacc cgccaacacc    7260
cgctgacgcg ccctgacggg cttgtctgct cccggcatcc gcttacagac aagctgtgac    7320
cgtctccggg agctgcatgt gtcagaggtt ttcaccgtca tcaccgaaac gcgcgaggca    7380
gggtgccttg atgtgggcgc cggcggtcga gtggcgacgg cgcggcttgt ccgcgccctg    7440
gtagattgcc tggccgtagg ccagccattt ttgagcggcc agcggccgcg ataggccgac    7500
gcgaagcggc ggggcgtagg gagcgcagcg accgaagggt aggcgctttt tgcagctctt    7560
cggctgtgcg ctggccagac agttatgcac aggccaggcg ggtttaagag ttttaataa     7620 gttttaaaga gttttaggcg gaaaaatcgc cttttttctc ttttatatca gtcacttaca    7680
tgtgtgaccg gttcccaatg tacgctttg ggttccaat gtacgggttc cggttcccaa     7740
tgtacggctt tgggttccca atgtacgtgc tatccacagg aaagagacct tttcgacctt    7800
tttcccctgc tagggcaatt tgccctagca tctgctccgt acattaggaa ccggcggatg    7860
cttcgccctc gatcaggttg cggtagcgca tgactaggat cgggccagcc tgccccgcct    7920
```

| | | | | |
|---|---|---|---|---|
| cctccttcaa | atcgtactcc | ggcaggtcat | ttgacccgat | cagcttgcgc | acggtgaaac | 7980 |
| agaacttctt | gaactctccg | gcgctgccac | tgcgttcgta | gatcgtcttg | aacaaccatc | 8040 |
| tggcttctgc | cttgcctgcg | gcgcggcgt | ccaggcggta | gagaaaacgg | ccgatgccgg | 8100 |
| gatcgatcaa | aaagtaatcg | gggtgaaccg | tcagcacgtc | cgggttcttg | ccttctgtga | 8160 |
| tctcgcggta | catccaatca | gctagctcga | tctcgatgta | ctccggccgc | ccggtttcgc | 8220 |
| tctttacgat | cttgtagcgg | ctaatcaagg | cttcaccctc | ggataccgtc | accaggcggc | 8280 |
| cgttcttggc | cttcttcgta | cgctgcatgg | caacgtgcgt | ggtgtttaac | cgaatgcagg | 8340 |
| tttctaccag | gtcgtctttc | tgcttccgc | catcggctcg | ccggcagaac | ttgagtacgt | 8400 |
| ccgcaacgtg | tggacggaac | acgcggccgg | gcttgtctcc | cttcccttcc | cggtatcggt | 8460 |
| tcatggattc | ggttagatgg | gaaaccgcca | tcagtaccag | gtcgtaatcc | cacacactgg | 8520 |
| ccatgccggc | cggccctgcg | gaaacctcta | cgtgcccgtc | tggaagctcg | tagcggatca | 8580 |
| cctcgccagc | tcgtcggtca | cgcttcgaca | gacggaaaac | ggccacgtcc | atgatgctgc | 8640 |
| gactatcgcg | ggtgcccacg | tcatagagca | tcggaacgaa | aaaatctggt | tgctcgtcgc | 8700 |
| ccttgggcgg | cttcctaatc | gacggcgcac | cggctgccgg | cggttgccgg | gattctttgc | 8760 |
| ggattcgatc | agcggccgct | tgccacgatt | caccggggcg | tgcttctgcc | tcgatgcgtt | 8820 |
| gccgctgggc | ggcctgcgcg | gccttcaact | tctccaccag | gtcatcaccc | agcgccgcgc | 8880 |
| cgatttgtac | cgggccggat | ggtttgcgac | cgtcacgccg | attcctcggg | cttggggt | 8940 |
| ccagtgccat | tgcagggccg | gcagacaacc | cagccgctta | cgcctggcca | accgccgtt | 9000 |
| cctccacaca | tggggcattc | cacggcgtcg | gtgcctggtt | gttcttgatt | ttccatgccg | 9060 |
| cctcctttag | ccgctaaaat | tcatctactc | atttattcat | ttgctcattt | actctggtag | 9120 |
| ctgcgcgatg | tattcagata | gcagctcggt | aatggtcttg | ccttggcgta | ccgcgtacat | 9180 |
| cttcagcttg | gtgtgatcct | ccgccggcaa | ctgaaagttg | acccgcttca | tggctggcgt | 9240 |
| gtctgccagg | ctggccaacg | ttgcagcctt | gctgctgcgt | gcgctcggac | ggccggcact | 9300 |
| tagcgtgttt | gtgcttttgc | tcattttctc | tttacctcat | taactcaaat | gagttttgat | 9360 |
| ttaatttcag | cggccagcgc | ctggacctcg | cgggcagcgt | cgccctcggg | ttctgattca | 9420 |
| agaacggttg | tgccggcggc | ggcagtgcct | gggtagctca | cgcgctgcgt | gatacgggac | 9480 |
| tcaagaatgg | gcagctcgta | cccggccagc | gcctcggcaa | cctcaccgcc | gatgcgcgtg | 9540 |
| cctttgatcg | cccgcgacac | gacaaaggcc | gcttgtagcc | ttccatccgt | gacctcaatg | 9600 |
| cgctgcttaa | ccagctccac | caggtcgcg | gtgggcccata | tgtcgtaagg | gcttggctgc | 9660 |
| accggaatca | gcacgaagtc | ggctgccttg | atcgcggaca | cagccaagtc | cgccgcctgg | 9720 |
| ggcgctccgt | cgatcactac | gaagtcgcgc | cggccgatgg | ccttcacgtc | gcggtcaatc | 9780 |
| gtcgggcggt | cgatgccgac | aacggttagc | ggttgatctt | cccgcacggc | cgcccaatcg | 9840 |
| cgggcactgc | cctggggatc | ggaatcgact | aacagaacat | cggccccggc | gagttgcagg | 9900 |
| gcgcgggcta | gatgggttgc | gatggtcgtc | ttgcctgacc | cgcctttctg | gttaagtaca | 9960 |
| gcgataacct | tcatgcgttc | cccttgcgta | tttgtttatt | tactcatcgc | atcatatacg | 10020 |
| cagcgaccgc | atgacgcaag | ctgttttact | caaatacaca | tcacctttt | agacggcggc | 10080 |
| gctcggtttc | ttcagcggcc | aagctggccg | gccaggccgc | cagcttggca | tcagacaaac | 10140 |
| cggccaggat | ttcatgcagc | cgcacggttg | agacgtgcgc | gggcggctcg | aacacgtacc | 10200 |
| cggccgcgat | catctccgcc | tcgatctctt | cggtaatgaa | aaacggttcg | tcctggccgt | 10260 |
| cctggtgcgg | tttcatgctt | gttcctcttg | gcgttcattc | tcggcggccg | ccagggcgtc | 10320 |

```
ggcctcggtc aatgcgtcct cacggaaggc accgcgccgc ctggcctcgg tgggcgtcac   10380
ttcctcgctg cgctcaagtg cgcggtacag ggtcgagcga tgcacgccaa gcagtgcagc   10440
cgcctctttc acggtgcggc cttcctggtc gatcagctcg cgggcgtgcg cgatctgtgc   10500
cggggtgagg gtagggcggg ggccaaactt cacgcctcgg gccttggcgg cctcgcgccc   10560
gctccgggtg cggtcgatga ttagggaacg ctcgaactcg gcaatgccgg cgaacacggt   10620
caacaccatg cggccggccg gcgtggtggt gtcggcccac ggctctgcca ggctacgcag   10680
gcccgcgccg gcctcctgga tgcgctcggc aatgtccagt aggtcgcggg tgctgcgggc   10740
caggcggtct agcctggtca ctgtcacaac gtcgccaggg cgtaggtggt caagcatcct   10800
ggccagctcc gggcggtcgc gcctggtgcc ggtgatcttc tcggaaaaca gcttggtgca   10860
gccggccgcg tgcagttcgg cccgttggtt ggtcaagtcc tggtcgtcgg tgctgacgcg   10920
ggcatagccc agcaggccag cggcggcgct cttgttcatg gcgtaatgtc tccggttcta   10980
gtcgcaagta ttctacttta tgcgactaaa acacgcgaca agaaaacgcc aggaaaaggg   11040
cagggcggca gcctgtcgcg taacttagga cttgtgcgac atgtcgtttt cagaagacgg   11100
ctgcactgaa cgtcagaagc cgactgcact atagcagcgg aggggttgga tcgatccctg   11160
ctcgcgcagg ctgggtgcca agctctcggg taacatcaag gcccgatcct tggagccctt   11220 gccctccgc acgatgatcg tgccgtgatc gaaatccaga tccttgaccc gcagttgcaa   11280
accctcactg atccgcatgc ccgttccata cagaagctgg gcgaacaaac gatgctcgcc   11340
ttccagaaaa ccgaggatgc gaaccacttc atccggggtc agcaccaccg gcaagcgccc   11400
ggacggccga ggtcttccga tctcctgaag ccagggcaga tccgtgcaca gcacttgccg   11460
tagaagaaca gcaaggccgc caatgcctga cgatgcgtgg agaccgaaac cttgcgctcg   11520
ttcgccagcc aggacagaaa tgcctcgact tcgctgctgc ccaaggttgc cgggtgacgc   11580
acaccgtgga aacggatgaa ggcacgaacc cagtggacat aagcctgttc ggttcgtaag   11640
ctgtaatgca agtagcgtat gcgctcacgc aactggtcca gaaccttgac cgaacgcagc   11700
ggtggtaacg gcgcagtggc ggttttcatg gcttgttatg actgtttttt tggggtacag   11760
tctatgcctc gggcatccaa gcagcaagcg cgttacgccg tgggtcgatg tttgatgtta   11820
tggagcagca acgatgttac gcagcagggc agtcgcccta aaacaaagtt aaacatcatg   11880
agggaagcgg tgatcgccga agtatcgact caactatcag aggtagttgg cgtcatcgag   11940
cgccatctcg aaccgacgtt gctggccgta catttgtacg gctccgcagt ggatggcggc   12000
ctgaagccac acagtgatat tgatttgctg gttacggtga ccgtaaggct tgatgaaaca   12060
acgcggcgag ctttgatcaa cgaccttttg gaaacttcgg cttcccctgg agagagcgag   12120
attctccgcg ctgtagaagt caccattgtt gtgcacgacg acatcattcc gtggcgttat   12180
ccagctaagc gcgaactgca atttggagaa tggcagcgca atgacattct tgcaggtatc   12240
ttcgagccag ccacgatcga cattgatctg gctatcttgc tgacaaaagc aagagaacat   12300
agcgttgcct tggtaggtcc agcggcggag gaactctttg atccggttcc tgaacaggat   12360
ctatttgagg cgctaaatga aaccttaacg ctatggaact cgccgcccga ctgggctggc   12420
gatgagcgaa atgtagtgct tacgttgtcc cgcatttggt acagcgcagt aaccggcaaa   12480
atcgcgccga aggatgtcgc tgccgactgg gcaatggagc gcctgccggc ccagtatcag   12540
cccgtcatac ttgaagctag acaggcttat cttggacaag aagaagatcg cttggcctcg   12600
cgcgcagatc agttggaaga atttgtccac tacgtgaaag gcgagatcac caaggtagtc   12660
```

```
ggcaaataat gtctaacaat tcgttcaagc cgacgccgct tcgcggcgcg gcttaactca  12720
agcgttagat gcactaagca cataattgct cacagccaaa ctatcaggtc aagtctgctt  12780
ttattatttt taagcgtgca taataagccc tacacaaatt gggagatata tcatgaaagg  12840
ctggcttttt cttgttatcg caatagttgg cgaagtaatc gcaacatccg cattaaaatc  12900
tagcgagggc tttactaagc tagcttgctt ggtcgttccg gtaccgtgaa cgtcggctcg  12960
attgtacctg cgttcaaata ctttgcgatc gtgttgcgcg cctgcccggt gcgtcggctg  13020
atctcacgga tcgactgctt ctctcgcaac gccatccgac ggatgatgtt taaaagtccc  13080
atgtggatca ctccgttgcc ccgtcgctca ccgtgttggg gggaaggtgc acatggctca  13140
gttctcaatg gaaattatct gcctaaccgg ctcagttctg cgtagaaacc aacatgcaag  13200
ctccaccggg tgcaaagcgg cagcgg                                        13226
```